US008492567B2

(12) United States Patent
Imbert et al.

(10) Patent No.: US 8,492,567 B2
(45) Date of Patent: Jul. 23, 2013

(54) (POLY)AMINOALKYLAMINOALKYLAMIDE, ALKYL-UREA, OR ALKYL-SULFONAMIDE DERIVATIVES OF EPIPODOPHYLLOTOXIN, A PROCESS FOR PREPARING THEM, AND APPLICATION THEREOF IN THERAPY AS ANTICANCER AGENTS

(75) Inventors: Thierry Imbert, Viviers les Montagnes (FR); Yves Guminski, Lagarrigue (FR); Jean-Marc Barret, Castres (FR); Anna Kruczynski, Pompertuzat (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 13/551,119

(22) Filed: Jul. 17, 2012

(65) Prior Publication Data
US 2012/0283281 A1    Nov. 8, 2012

Related U.S. Application Data

(62) Division of application No. 12/737,645, filed as application No. PCT/EP2009/060739 on Aug. 19, 2009, now Pat. No. 8,288,567.

(30) Foreign Application Priority Data

Aug. 19, 2008    (FR) ...................... 08 55629

(51) Int. Cl.
C07D 307/77    (2006.01)
A01N 43/78    (2006.01)
A01N 43/26    (2006.01)

(52) U.S. Cl.
USPC ........................... 549/298; 514/274; 514/463

(58) Field of Classification Search
USPC .................. 549/298; 514/274, 463
See application file for complete search history.

(56) References Cited

U.S. PATENT DOCUMENTS

| | | | |
|---|---|---|---|
| 5,300,500 | A | 4/1994 | Lee et al. |
| 6,008,382 | A | 12/1999 | Imbert et al. |
| 6,566,393 | B1 | 5/2003 | Lee et al. |
| 7,378,419 | B2 | 5/2008 | Monneret et al. |
| 2004/0101574 | A1 | 5/2004 | Monneret et al. |
| 2004/0106676 | A1 | 6/2004 | Lee et al. |
| 2009/0137826 | A1 | 5/2009 | Guminski et al. |

FOREIGN PATENT DOCUMENTS

| | | |
|---|---|---|
| EP | 0876374 B1 | 7/2002 |
| FR | 2742439 A1 | 6/1997 |
| FR | 2810321 A1 | 12/2001 |
| FR | 2921369 A1 | 3/2009 |
| WO | WO 03/082876 A1 | 10/2003 |
| WO | WO 2004/000859 A2 | 12/2003 |
| WO | WO 2004/073375 A2 | 9/2004 |
| WO | WO 2004073375 * | 9/2004 |
| WO | WO 2005/100363 A1 | 10/2005 |
| WO | WO 2007/010007 A1 | 1/2007 |
| WO | WO 2009/050365 A2 | 4/2009 |
| WO | WO 2005100363 * | 1/2012 |

OTHER PUBLICATIONS

Wang et al. Acta pharmaceutica Sinica Feb. 1993; 28(6):422-7.*
Miyahara et al. Heterocycles, 1994, 39(1), 361-369.*
Xiao et al. Journal of Medicinal Chemistry, 2002, 45, 2294-2309.*
Duca et al. Org.Biomol.Chem., 2005, 3, 1074-1080.*
"TOP-53—Antineoplastic Podphyllotoxin DNA Topoisomerase II Inhibitor," Manufacturer; Taiho Pharmaceuticals Co., Ltd. (JP), Drugs of the Future, vol. 21, No. 11, 1996, pp. 1136-1139.
Blagbrough et al., "Practical Synthesis of the Putative Polyamine Spider Toxin FTX: a Proposed Blocker of Voltage-Sensitive Calcium Channels," Tetrahedron Letters, vol. 35, No. 13. 1994, pp. 2057-2060.
Blagbrough et al., "Practical Synthesis of Unsymmetrical Polyamine Amides," Tetrahedron Letters, vol. 39, 1998, pp. 439-442.
Constantinou-Kokutou et al., "Synthesis of 1,3-Diamines," OPPI Briefs, vol. 26, No. 5, 1994, pp. 599-602.
Delcros et al., "Effect of Spermine Conjugation on the Cytotoxicity and Cellular Transport of Acridine," J. Med. Chem, vol. 45, 2002, pp. 5098-5111.
Duca et al., "Novel carbamate derivatives of 4-β-Amino-4'-O-demethyl-4-desoxypodophyllotoxin as inhibitors of topoisomerase II: synthesis and biological evaluation," Org. Biomol. Chem., vol. 3, 2005. pp. 1074-1080.
Durand et al., °(−)-15-Deoxyspergualin: A New and Efficient Enantioselective Synthesis Which Allows the Definitive Assignment of the Absolute Configuration, J. Org. Chem., vol. 63, 1998, pp. 9723-9727.
Gardner et al., "N1-Substituent Effects in the Selective Delivery of Polyamine Conjugates into Cells Containing Active Polyamine Transporters," J. Med. Chem., vol. 47, 2004, pp. 6055-6069.
Geall et al., "Homologation of Polyamines in the Rapid Synthesis of Lipospermine Conjugates and Related Lipoplexes," Tetrahedron, vol. 56, 2000, pp. 2449-2460.
Geall et al., "Homologation of Polyamines in the Synthesis of Lipo-Spermine Conjugates and related Lipoplexes," Tetrahedron Letters, vol. 39, 1998, pp. 443-446.
Guianvarc'h et al., "Synthesis and Biological Activity of Sulfonamide Derivatives of Epipodophyllotoxin," J. Med. Chem., vol. 47, 2004, pp. 2374.
Hansen et al., "New Compounds Related to Podophyllotoxin and Congeners: Synthesis, Structure Elucidation and Biological Testing," Acta Chemica Scandinavica, vol. 47, 1993, pp. 1190-1200.
International Search Report, dated Jan. 21, 2010, for International Application No. PCT/EP2009/060739.

(Continued)

*Primary Examiner* — Nizal Chandrakumar
(74) *Attorney, Agent, or Firm* — Birch, Stewart, Kolasch & Birch, LLP

(57) ABSTRACT

The present invention relates to new derivatives of epipodophyllotoxin 4-substituted with an optionally substituted (poly)aminoalkylaminoalkylamide, or alkyl-urea or alkyl-sulfonamide chain, a process for preparing them and their use as a medicine as an anticancer agent.

10 Claims, No Drawings

OTHER PUBLICATIONS

Kamal et al., "Synthesis of 4β-amido and 4β-sulphonamido Analogues of Podophyllotoxin as Potential Antitimour Agents," Bioorganic & Medicinal Chemistry, vol. 11, 2003, pp. 5135-5142.

Kramer et al., "Regulation of Polyamine Transport by Polyamines and Polyamine Analogs,"Journal of Cellular Physiology, vol. 155, No. 2, 1993, pp. 399-407.

Kruczynski et al., "Preclinical in vivo antitumor activity of vinflunine, a novel fluorinated Vinca alkaloid," Cancer Chemother. Pharmacol., vol. 41, 1998, pp. 437-447.

Langdon et al., "Preclinical phase II studies in human tumor xenografts: A European multicenter follow-up study," Annals of Oncology, vol. 5, 1994, pp. 415-422.

Lee et al., "An efficient and practical method for the synthesis of mom-N-protected α,ω-diaminoalkanes," Tetrahedron Letters, vol. 42, 2001, pp. 2709-2711.

Levchine et al., "An Efficient Synthesis of Selectively Functionalized Spermidine," Synthesis, Jan. 1994, pp. 37-39.

Marton et al., "Polyamines as Targets for Therapeutic intervention," Annu. Rev. Pharmacol. Toxicol., vol. 35, 1995. pp. 55-91.

Miyahara et al., "Nitrosourea Derivatives of 3',4'-Didemethoxy-3',4'-Dioxo-4-Deoxypodophyllotoxin and Urea Derivatives of 4'-O-Demethylpodophyllotoxin as Potent Inhibitors of Human DNA Topoisomerase II1," Heterocycles, vol. 39, No. 1, 1994. pp. 361-369.

Moya et al., "Rapid, Practical Syntheses of the Arginyl Polyamine sFTX-3,3: a Blocker of Voltage-Sensitive Calcium Channels," Tetrahedron Letters, vol. 35, No. 13, 1994, pp. 2061-2062.

Moya et al., "Total Syntheses of Polyamine Amides PhTX-4.3.3 and PhTX-3.4.3: Reductive Alkylation is a Rapid, Practical Route to Philanthotoxins," Tetrahedron Letters, vol. 36, No. 51, 1995, pp. 9401-9404.

Mross et al., "Pharmacokinetics and pharmacodynamics of the new podophyllotoxin derivative NK 611—A study by the AIO groups PHASE-I and APOH," Cancer Chemother. Pharmacol., vol. 38, 1996, pp. 217-224.

Nagarajan et al., "Design, Synthesis, and Biological Evaluation of Indenoisoquinoline Topoisomerase I Inhibitors Featuring Polyamine Side Chains on the Lactam Nitrogen," J. Med. Chem., vol. 46, No. 26, 2003, pp. 5712-5724.

Najer et al., "No. 112—Sur quelques amino-2 dihydro-5,6 oxazines-1,3 N-substituées." Bull. Soc. Chim. Fr., 1959, pp. 611-612 (English abstract/summary provided).

Nihei et al., "An efficient and versatile synthesis of all structural types of acylpolyamine spider toxins," Tetrahedron, vol. 62, 2006, pp. 8335-8350.

Phanstiel., IV et al., "The Effect of Polyamine Homologation on the Transport and Cytotoxicity Properties of Polyamine—(DNA-Intercalator) Conjugates," J. Org. Chem., vol. 65, 2000, pp. 5590-5599.

Pittelkow et al., "Selective Synthesis of Carbamate Protected Polyamines Using Alkyl Phenyl Carbonates," Synthesus, No. 15, Print 29, 2002, pp. 2195-2202.

Rothenborg-Jensen et al., "Linker length in podophyllotoxin-acridine conjugates determines potency in vivo and in vitro as well as specificity against MDR cell lines," Anti-Cancer Drug Design, vol. 16, 2001, pp. 305-315.

Seiler et al., "Les polyamines présentent-ellers un intérêt dans le traitment du cancer?", Médecine/Science, Synthèse, vol. 12, 1996, pp. 745-755 (including English summary—Why are polyamines of interest to cancerologists?).

Tabor et al., "Polyamines," Ann. Rev. Biochem., vol.53, 1984, pp. 749-790.

Venditti, "Preclinical Drug Development: Rationale and Methods," Seminars in Oncology, vol. 8, No. 4, Dec. 1981, pp. 349-361.

Wakamiya et al., "Design and Synthesis of Peptides Passing through the Blood-Brain Barrier," Bull. Chem Soc. Jpn., vol. 71, 1998, pp. 699-709.

Wang et al., "Recent Advances in the Discovery and Development of Topoisomerase Inhibitors as Antitumor Agents," Medicinal Research Reviews, vol. 17, No. 4, 1997, pp. 367-425 (pp. 367-423 provided).

Wang et al., "Synthesis and Antitumor Activities of 4-Acylamido-4-Deoxy-4'-Demethylepipodophyliotoxin Analogues," Acta Pharmacetica Sinica, vol. 28, No. 6, 1993, pp. 422-427 (including English abstract).

Xiao et al., "Antitumor Agents. 213, Modeling of Epipodophyllotoxin Derivatives Using Variable Selection κ Nearest Neighbor QSAR Method," J. Med. Chem, vol. 45, 2002, pp. 2294-2309.

Zhou et al., "Antitumor Agents, 120. New 4-Subsituted Benzylamine and Benzyl Ether Derivatives of 4'-O-Demethylepipodophyollotoxin as Potent Inhibitors of Human DNA Topoisomerase II," J. Med. Chem., vol. 34, 1991, pp. 3346-3350.

* cited by examiner

(POLY)AMINOALKYLAMINOALKYLAMIDE, ALKYL-UREA, OR ALKYL-SULFONAMIDE DERIVATIVES OF EPIPODOPHYLLOTOXIN, A PROCESS FOR PREPARING THEM, AND APPLICATION THEREOF IN THERAPY AS ANTICANCER AGENTS

CROSS REFERENCE TO RELATED APPLICATIONS

This application is a Divisional of application Ser. No. 12/737,645 filed on Feb. 2, 2011, now U.S. Pat. No. 8,288,567, which is a National Phase of PCT International Application No. PCT/EP2009/060739 filed on Aug. 19, 2009, which claims the benefit of Patent Application No. 0855629 filed in FRANCE, on Aug. 19, 2008. The entire contents of all of the above applications is hereby incorporated by reference.

The present invention relates to new derivatives of podophyllotoxin 4-substituted with an optionally substituted (poly)aminoalkylaminoalkylamide or alkyl-sulfonamide or alkyl-urea chain, a process for preparing them and their use as a medicine, in particular as anticancer agents.

The compounds of the present invention are derived from podophyllotoxin, a natural lignane known as a therapeutic agent in the treatment of cancer. Other synthetic derivatives such as etoposide or teniposide are part of the therapeutic arsenal for the treatment of small cell lung cancer in particular. These various compounds act by inhibiting the catalyst activity of topoisomerase II.

The alkylamine substitution in the 4β-position of the 4'-demethylpodophyllotoxin backbone thus represents a spermine or spermidine alkylamide unit, or more generally a (poly)aminoalkylaminoalkylamide unit. Likewise this substitution represents a spermine or spermidine alkyl-sulfonamide unit, or more generally a (poly)aminoalkyaminoalkylsulfonamide unit. Further, this substitution represents a spermine or spermidine alkylurea unit, or more generally a (poly)aminoalkylaminoalkylurea unit.

The 4'-demethylepipodophyllotoxin derivatives are known as 2-topoisomerase inhibitors. Their cytotoxic and antitumor activities have been discovered and revealed, in particular with etoposide, TOP 53 (*Drugs of the Future* 1996, 21, 1136), GL 331 (*Medicinal Research Reviews*, 1997, 17, 367), and NK 611 (*Cancer Chemother. Pharmacol.* 1996, 38, 217 and 541). Compounds having benzylamine-type amine chains directly linked to the 4β-position of the podophyllotoxin have been described (*J. Med. Chem.* 1991, 34, 3346). Patent application FR 2 810 321 discloses carbamate- or thiocarbamate-type podophyllotoxin derivatives useful in the treatment of cancer. Amide compounds in the 4β-position have also been described (U.S. Pat. No. 6,566,393; *Acta Pharmaceutica Sinica* (*Yaoxue Xuebao*), 1993, 28, 422; *Acta Chem. Scand.* 1993, 47, 1190; *Anti-Cancer Drug Design* 2001, 16, 305). Urea compounds in the 4β-position have been described (*Heterocycles* 1994, 39, (1), 361; *J. Med. Chem.* 2002, 45, 2294).

The patent EP 0 876 374 discloses a process for demethylating podophyllotoxin and readily gives the 4'-demethylepipodophyllotoxin, which is a synthesis intermediate in the preparation of etoposide and teniposide.

The international application WO 03/082876 discloses 4β-4''-[{2''-benzoyl substituted}anilino] derivatives of podophyllotoxin having an anticancer activity.

The need to provide more effective treatments encourages the search for new molecules having various mechanisms of action, thereby targeting currently badly treated or non-treated types of tumors, as well as avoiding resistance problems. The availability of these new products also allows to develop protocols including co-treatments, which are more active on some tumors.

The new compounds of the present invention provide a way to overcome this problem.

Compounds described in patent application WO 2005/100363 have an acetamide moiety in the 4β-position of the podophyllotoxin unit, said moiety being linked to an amine or polyamine chain. We have synthesized other derivatives having an alkylamide, urea or sulfonamide moiety and documented their cytotoxic and anticancer activity.

The present invention relates to compounds of the general formula 1:

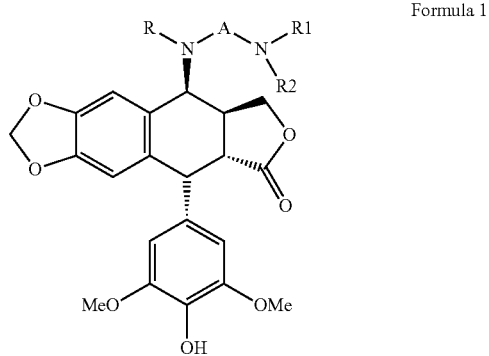

Formula 1 wherein
R represents hydrogen or $C_{1-4}$alkyl,
A represents $CO(CH_2)_n$, where n=2, 3, 4, or 5, or
A represents $CONH(CH_2)_n$, where n has the same values as described above, or
A represents $SO_2(CH_2)_n$, where n has the same values as described above,
R1=H, or $C_{1-4}$alkyl,
R2=H, or $C_{1-4}$alkyl, or
R2 can also be $(CH_2)_m$—NR3R4, where R3=H, or $C_{1-4}$alkyl, and m=2, 3, 4, or 5,
R4=H, or $C_{1-4}$alkyl, or
R4 can also be $(CH_2)_p$—NR5R6, where R5=H, or $C_{1-4}$alkyl, and p=2, 3, 4, or 5, and
R6=H, or $C_{1-4}$alkyl, or
R6 can also be $(CH_2)_q$—$NH_2$, where q=2, 3, 4, or 5,
with the exception of the compound wherein A=$CO(CH_2)_2$ where R1=R2=H.

The term <<$C_{1-4}$alkyl>>, as defined in the present invention, is meant to refer to a saturated, linear or branched, hydrocarbon chain comprising 1 to 4 carbon atoms. An example includes methyl, ethyl, propyl, isopropyl, butyl, isobutyl, sec-butyl, and tert-butyl groups. Thus, throughout this specification, $C_3$ and $C_4$ alkyl groups designate both linear and branched groups.

The invention also relates to their salts, particularly their pharmaceutically acceptable water-soluble salts, especially inorganic or organic acid addition salts thereof, as well as pharmaceutical compositions containing them, and their use as a medicine, in particular intended for treating cancer.

Urea, amide, carbamate or sulfonamide podophyllotoxin derivatives have been described in the literature and in patents (*Zhongguo Yaoke Daxue Xuebao* 1993, 24, 134; WO 2004/000859; US 2004/0106676; *J. Med. Chem.* 2004, 47, 2365; *Org. Biomol. Chem.* 2005, 3, 1074; WO 2004/073375; *Bioorg. Med. Chem.* 2003, 11, 5135). Their activity indicates an inhibiting action on 2-topoisomerase and a value as a compound having an antitumor activity. However the low water-solubility of these compounds makes them difficult to use. While a basic nitrogen atom present in the molecule makes it optionally possible to prepare a soluble salt, it is not always obvious to achieve an active compound having the required antitumor properties.

The literature does not disclose any compound having a polyamine chain grafted in the 4β-position of the 4'-demethyl-4-deoxypodophyllotoxin, through a spacer, with the exception of patent application WO 2005/100363.

Accordingly the present invention discloses new polyamine derivatives derived from podophyllotoxin.

The compounds of the present invention have an epipodophyllotoxin structure substituted in the 4β-position with a urea unit linked to a polyamine chain such as in particular putrescine, spermine or spermidine, but also other polyamines. Likewise this 4β-position can be linked to an amide group, whether the latter is linked or not to a linear spacer having 2 to 5 carbon atoms then to a polyamine such as putrescine, spermine or spermidine or other polyamines.

The 4β-position can be also substituted with a sulfamidoethyl unit linked in turn to a polyamine chain such as putrescine, spermine or spermidine. The polyamine transportation system has already been utilized for targeting cytotoxic polyamine analogs (*Annu. Rev. Pharmacol. Toxicol.* 1995, 35, 55; *Medicine/Sciences* 1996, 12, 745), but seemingly without success.

Compounds having a polyamine chain grafted on a DNA intercalating unit of the acridine (*J. Org. Chem.* 2000, 65, 5590; *J. Med. Chem.* 2002, 45, 5098), or indenoisoquinoline (*J. Med. Chem.* 2003, 46, 5712) type have been described.

The property of the compounds of the present invention is that they are DNA targeting agents, and successfully induce damages within said DNA, both qualitatively and quantitatively different from the other known anticancer compounds such as etoposide.

The presence of a polyamine chain, such as for example putrescine, spermine or spermidine, is advantageous in that it is recognized by the transportation system of natural polyamines used by the cancer cell to proliferate (*J. Cell. Physiol.* 1993, 155, 399; *Annu. Rev. Biochem.* 1984, 53, 749). This provides the compounds of the present invention with a preferred passage way towards the cancer cell preferentially compared with other cells. The compounds of the present invention thus have in vitro cytotoxic properties and in vivo antitumor properties.

Furthermore, an important advantage of these compounds is the presence of amine functions providing a good water solubility, which makes them convenient in terms of formulation, administration, dispensing ability, and bioavailability in the body. The pharmacokinetic parameters are thus improved.

The preferred compounds of the invention are selected from the following compounds:

Amide Series:

Compound 1: 3-(2-Dimethylaminoethylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide

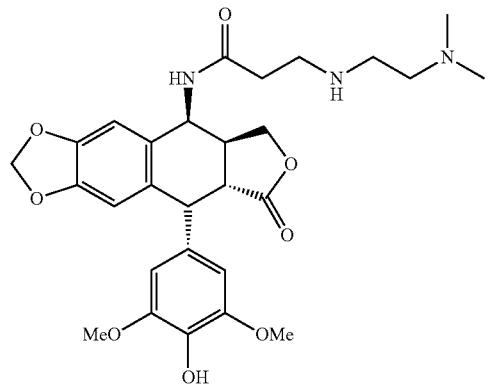

Compound 2: 4-(2-Dimethylaminoethylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide

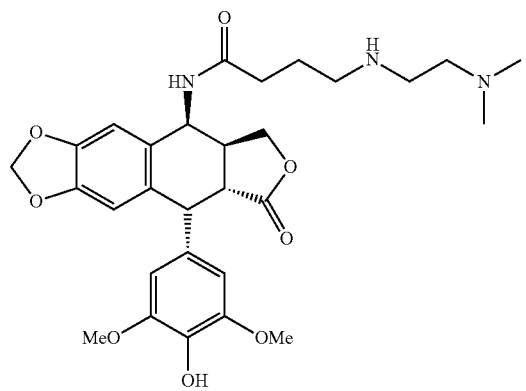

Compound 3: 3-[(2-Dimethylaminoethyl)-methylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide

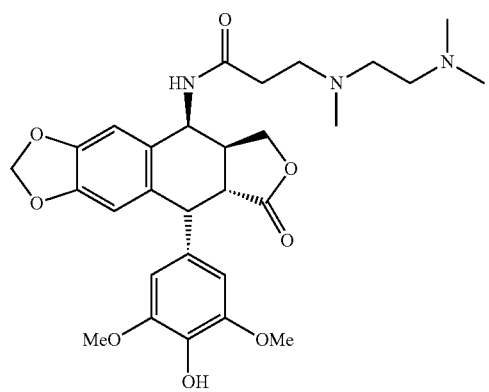

Compound 4: 4-[(2-Dimethylaminoethyl)-methy-lamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide

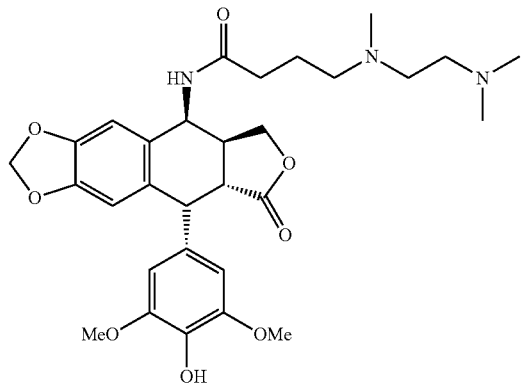

Compound 5: 3-Dimethylamino-N-[9-(4-hydroxy-3,5-dimethoxyphenyl)-8-oxo-5,5a,6,8,8a,9-hexahydro-furo[3',4':6,7]naphtho[2,3-d][1,3]dioxol-5-yl]-propionamide

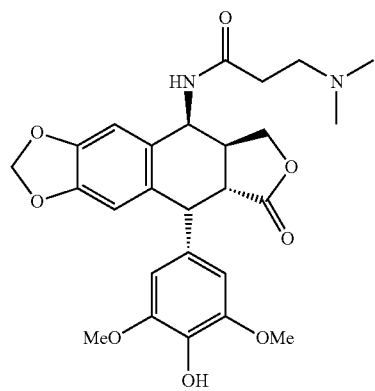

Compound 6: 4-Dimethylamino-N-[9-(4-hydroxy-3,5-dimethoxyphenyl)-8-oxo-5,5a,6,8,8a,9-hexahydro-furo[3',4':6,7]naphtho[2,3-d][1,3]dioxol-5-yl]-butyramide

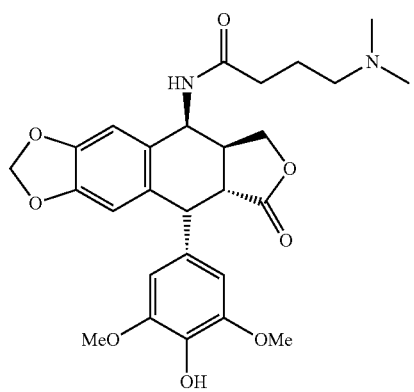

Compound 7: 5-Dimethylaminopentanoic acid N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-amide

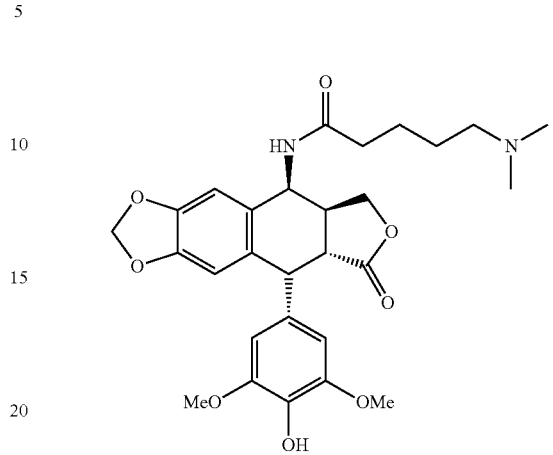

Compound 8: 3-(2-Diethylaminoethylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide

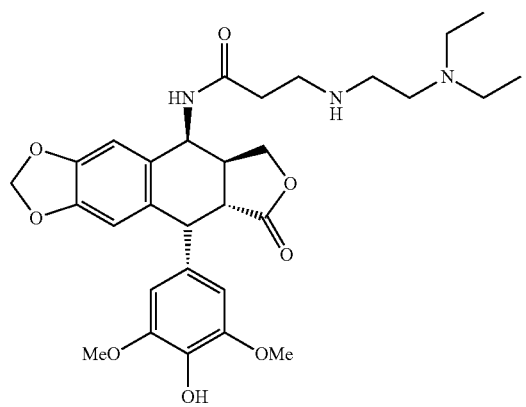

Compound 9: 4-(2-Diethylaminoethylamino)-N-[9-(4-hydroxy-3,5-dimethoxyphenyl)-8-oxo-5,5a,8a,9-hexahydrofuro[3',4':6,7]naphtho[2,3-d][1,3]dioxol-5-yl]-butyramide

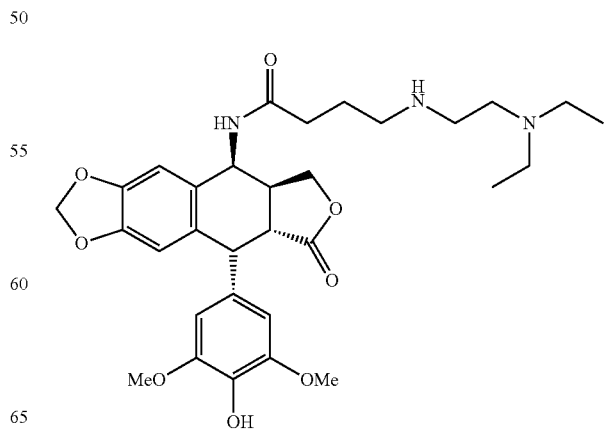

Compound 10: 3-(2-Diethylaminopropylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide

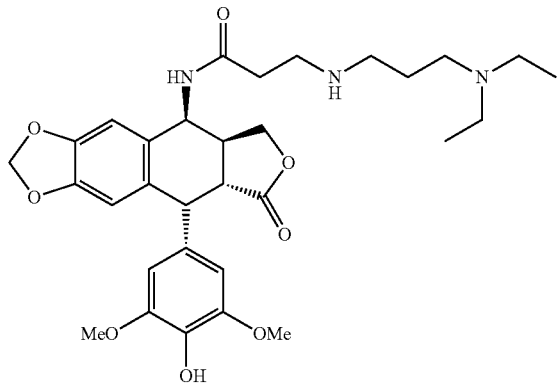

Compound 11: 4-(2-Diethylaminopropylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide

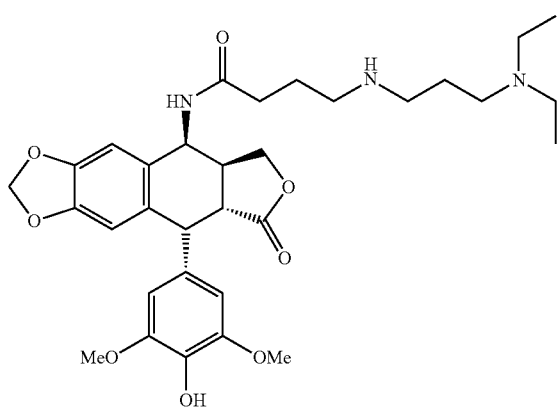

Compound 12: 3-(2-Aminoethylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide

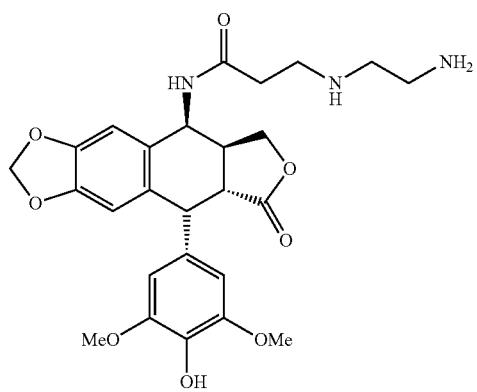

Compound 13: 3-(3-Aminopropylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide

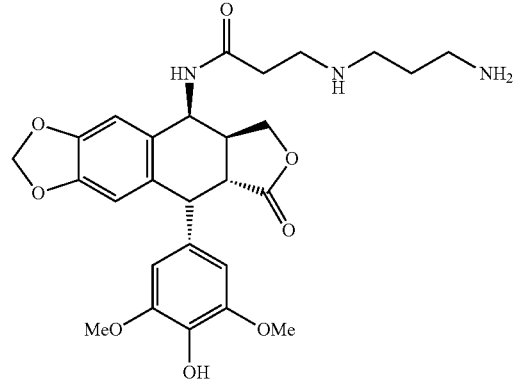

Compound 14: 3-(4-Aminobutylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide

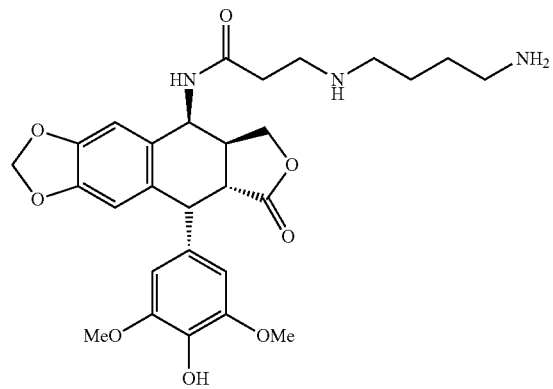

Compound 15: 4-(3-Aminopropylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide

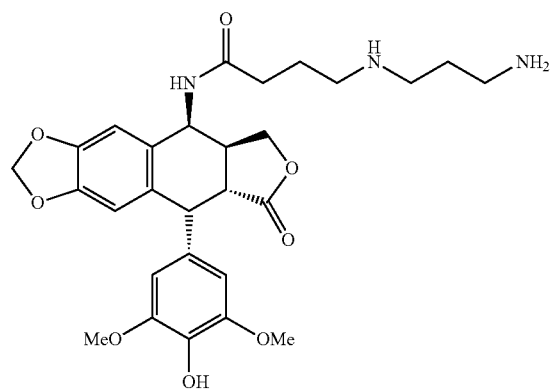

Compound 16: 4-(4-Aminobutylamino)-N-[9-(4-hydroxy-3,5-dimethoxyphenyl)-8-oxo-5,5a,6,8,8a,9-hexahydro furo[3',4':6,7]naphtho[2,3-d][1,3]dioxol-5-yl]-butyramide

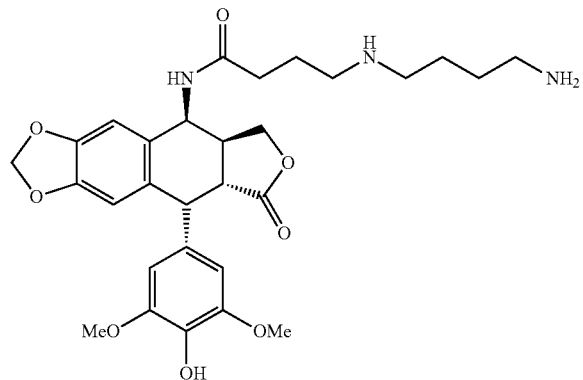

Compound 17: 5-(4-Aminobutylamino)pentanoic acid N-[9-(4-hydroxy-3,5-dimethoxyphenyl)-8-oxo-5,5a,6,8,8a,9-hexahydrofuro[3',4':6,7]naphtho[2,3-d][1,3]-dioxol-5-yl]-amide

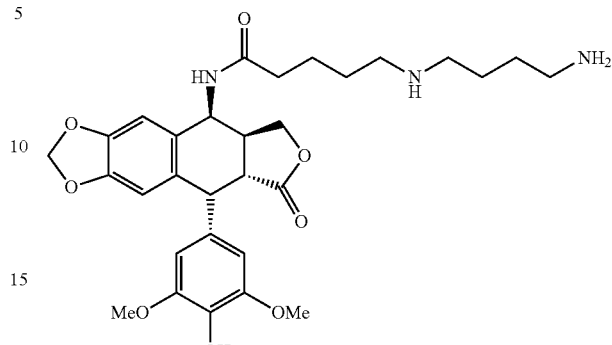

Compound 18: 3-{3-[4-(3-Aminopropylamino)-butylamino]-propylamino}-N-[9-(4-hydroxy-3,5-dimethoxyphenyl)-8-oxo-5,5a,6,8,8a,9-hexahydro-furo[3',4':6,7]-naphtho[2,3-d][1,3]dioxol-5-yl]-propionamide

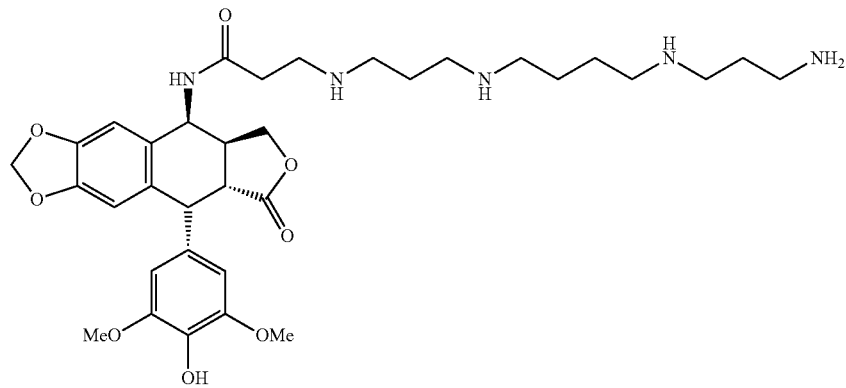

Compound 19: 3-{3-[3-(3-Aminopropylamino)-propylamino]-propylamino}-N-[9-(4-hydroxy-3,5-dimethoxyphenyl)-8-oxo-5,5a,6,8,8a,9-hexahydro-furo[3',4':6,7]-naphtho[2,3-d][1,3]dioxol-5-yl]-propionamide

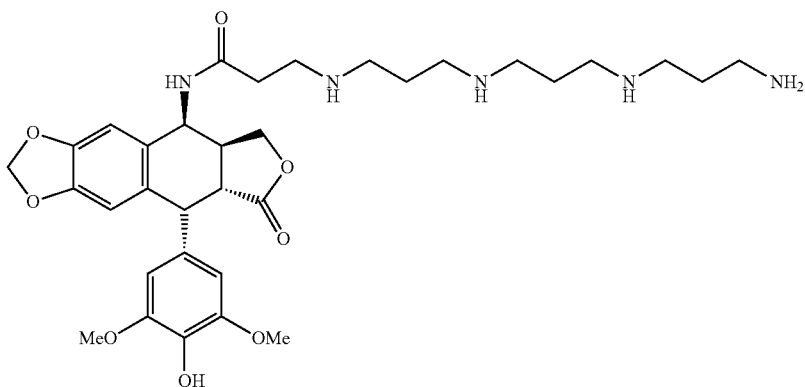

Compound 20: 3-{4-[4-(4-Aminobutylamino)-butylamino]-butylamino}-N-[9-(4-hydroxy-3,5-dimethoxyphenyl)-8-oxo-5,5a,6,8,8a,9-hexahydro-furo-[3',4':6,7]naphtho[2,3-d][1,3]dioxol-5-yl]-propionamide

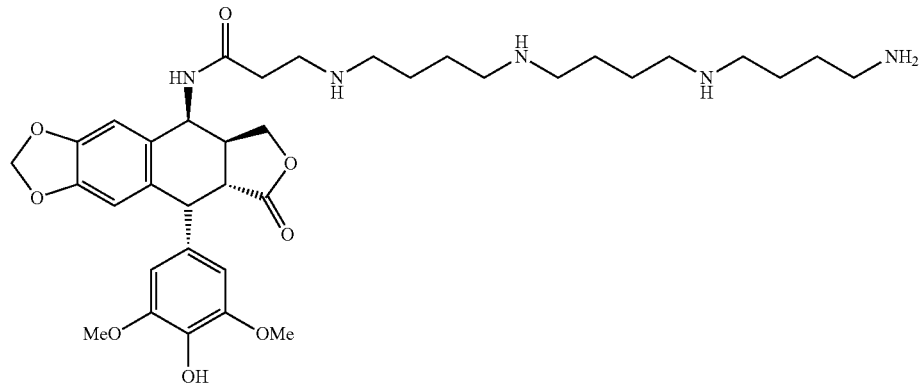

Compound 21: 4-{3-[4-(3-Aminopropylamino)-butylamino]-propylamino}-N-[9-(4-hydroxy-3,5-dimethoxyphenyl)-8-oxo-5,5a,6,8,8a,9-hexahydro-furo[3',4':6,7]-naphtho[2,3-d][1,3]dioxol-5-yl]-butyramide

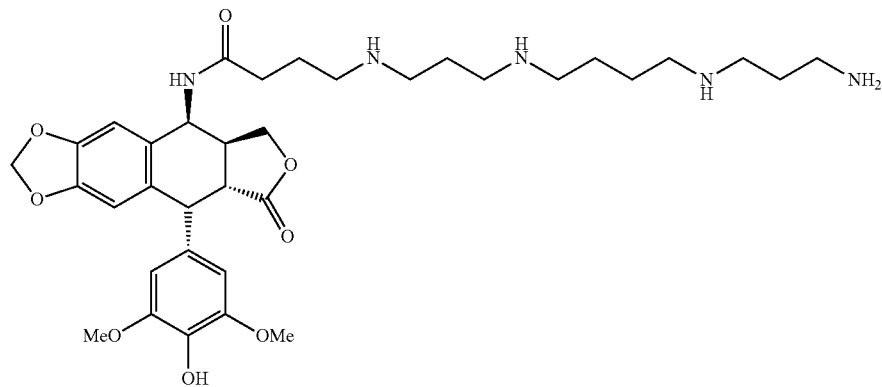

Compound 22: 4-{3-[3-(3-Aminopropylamino)-propylamino]-propylamino}-N-[9-(4-hydroxy-3,5-dimethoxyphenyl)-8-oxo-5,5a,6,8,8a,9-hexahydro-furo-[3',4':6,7]naphtho[2,3-d][1,3]dioxol-5-yl]-butyramide

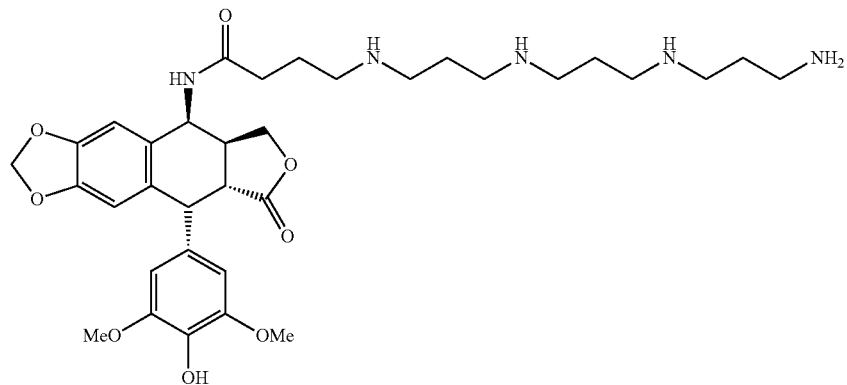

Compound 23: 4-{4-[4-(4-Aminobutylamino)-butylamino]-butylamino}-N-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-butyramide

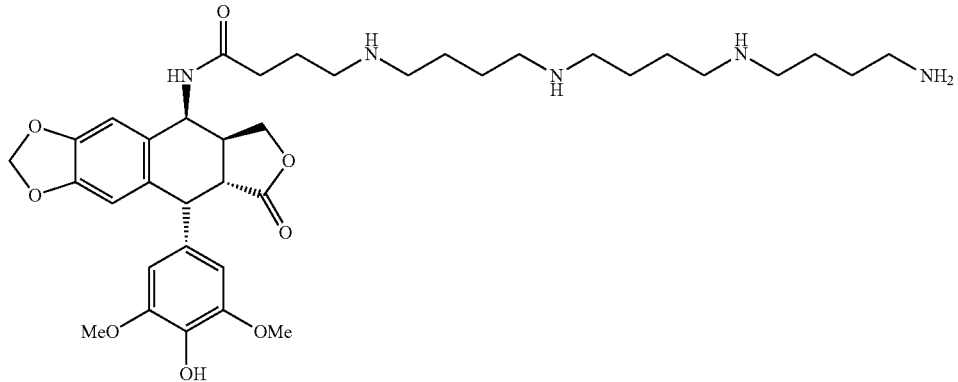

Compound 24: 5-{3-[4-(3-Aminopropylamino)-butylamino]-propylamino}pentanoic acid N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-amide

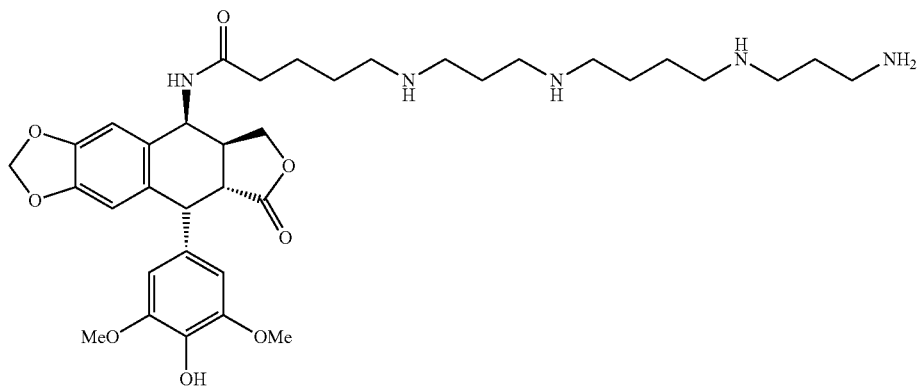

Compound 25: 5-{3-[3-(3-Aminopropylamino)-propylamino]-propylamino}pentanoic acid N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-amide

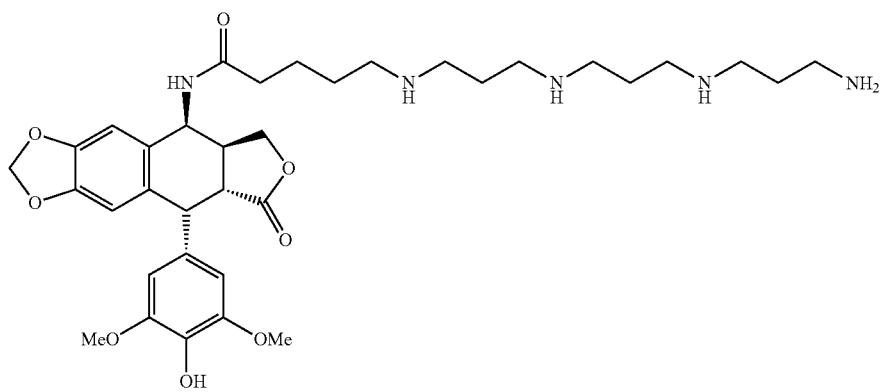

Compound 26: 5-{4-[4-(4-Aminobutylamino)-butylamino]-butylamino}pentanoic acid N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-amide

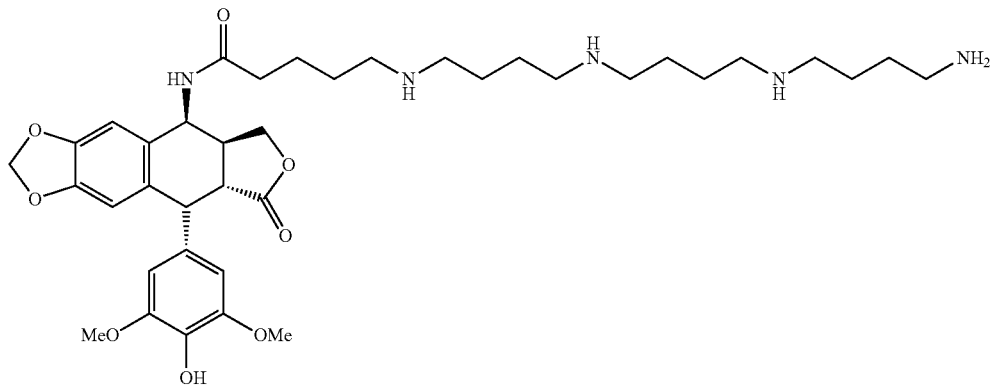

Compound 27: 3-[3-(4-Aminobutylamino)-propylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide

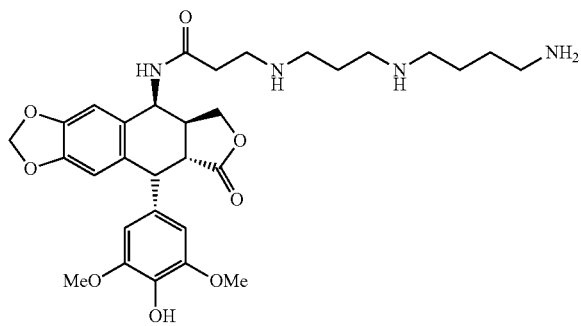

Compound 28: 3-[4-(3-Aminopropylamino)-butylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide

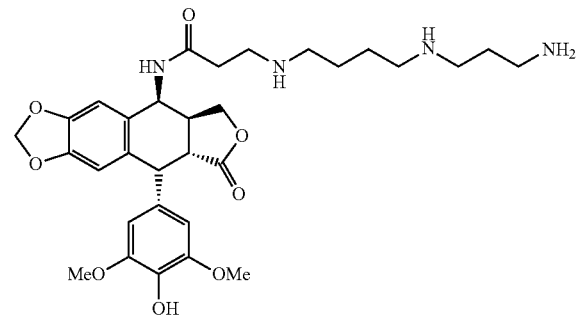

Compound 29: 3-[3-(3-Aminopropylamino)-propylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide

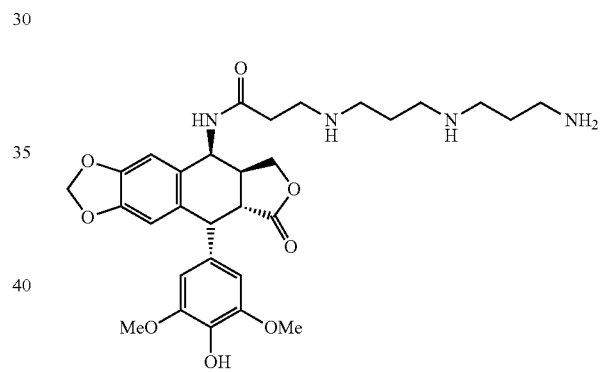

Compound 30: 3-[4-(4-Aminobutylamino)-butylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide

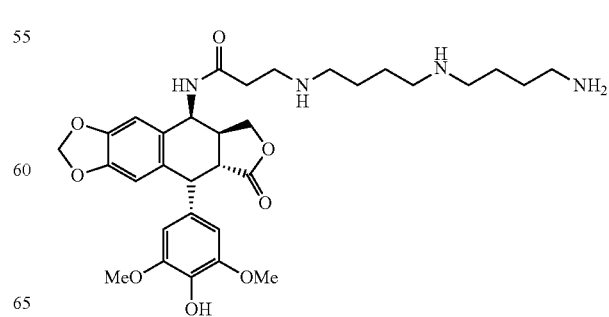

Compound 31: 4-[3-(4-Aminobutylamino)-propylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide

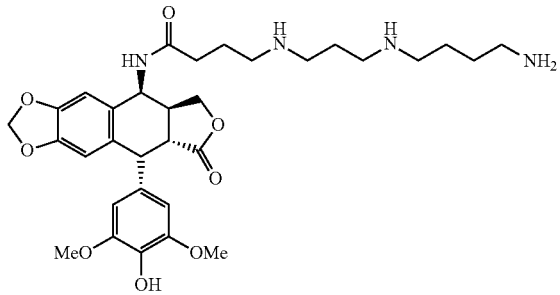

Compound 33: 4-[3-(3-Aminopropylamino)-propylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide

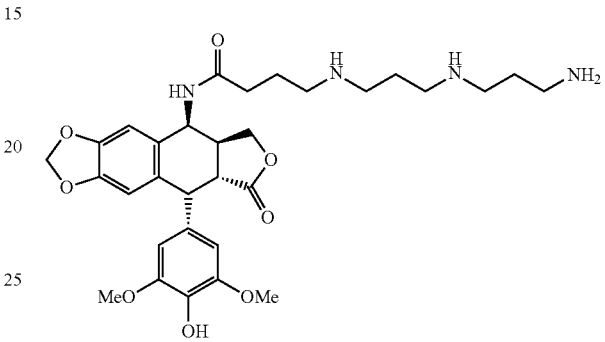

Compound 32: 4-[4-(3-Aminopropylamino)-butylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide

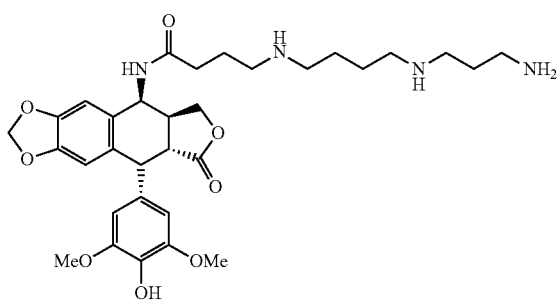

Compound 34: 4-[4-(4-Aminobutylamino)-butylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide

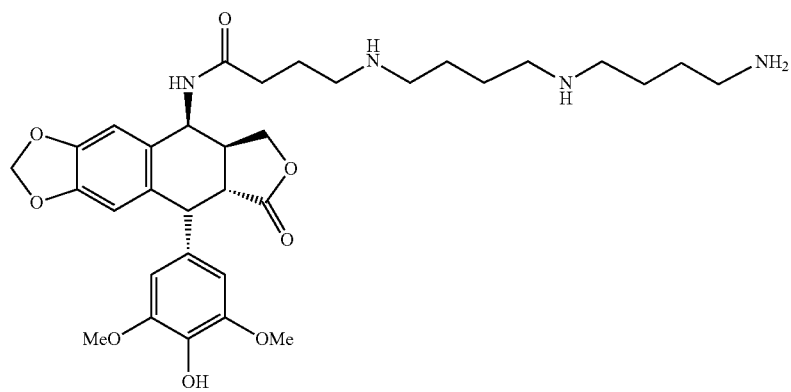

Compound 35: 5-[3-(4-Aminobutylamino)-propylamino]pentanoic acid N-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-amide

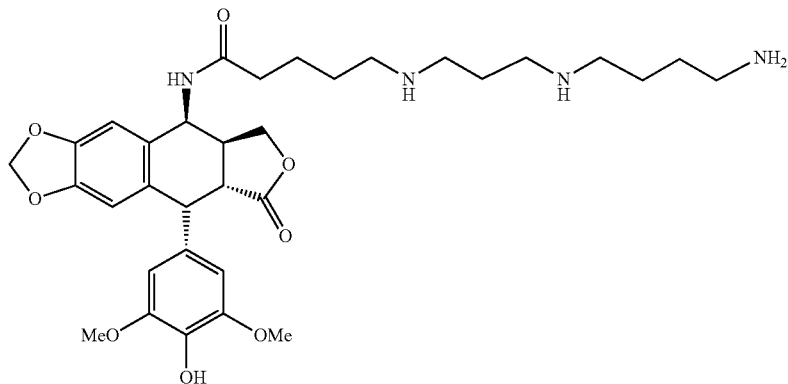

Compound 36: 5-[4-(3-Aminopropylamino)-butylamino]pentanoic acid N-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-amide

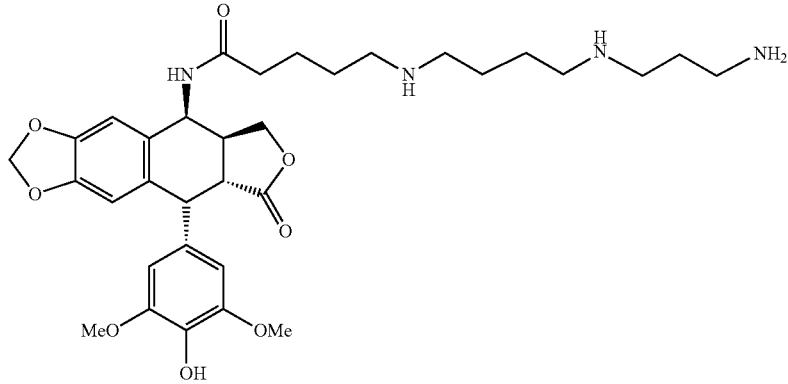

Compound 37: 5-[3-(3-Aminopropylamino)-propylamino]pentanoic acid N-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-amide

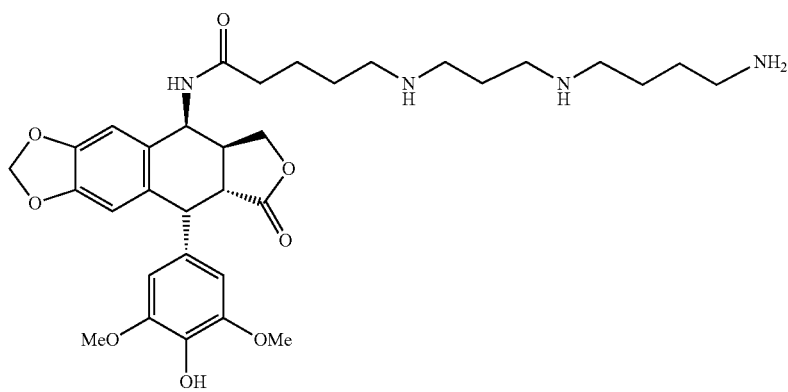

Compound 38: 5-[4-(4-Aminobutylamino)-butylamino]pentanoic acid N-[9-(4-hydroxy-3,5-dimethoxyphenyl)-8-oxo-5,5a,6,8,8a,9-hexahydrofuro[3',4':6,7]naphtha-[2,3-d][1,3]dioxol-5-yl]-amide

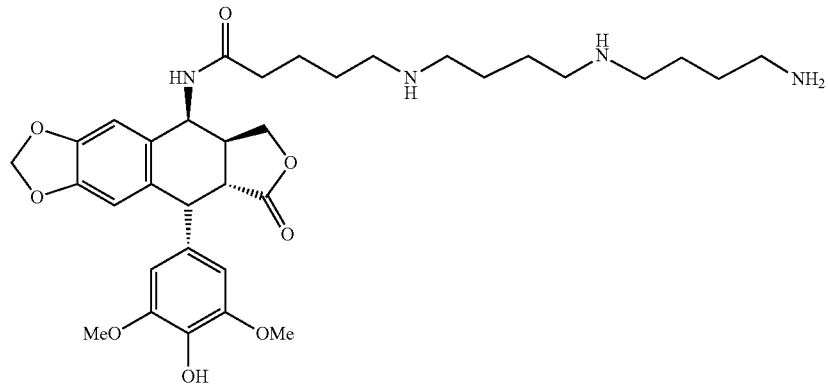

Compound 55: 5-[(2-Dimethylaminoethyl)-methylamino]pentanoic acid N-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-amide

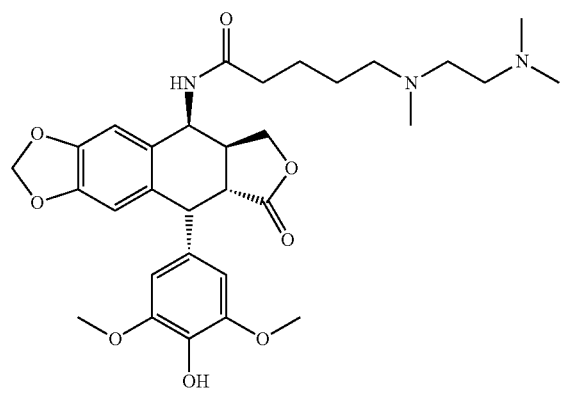

Compound 56: 4-Amino-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide

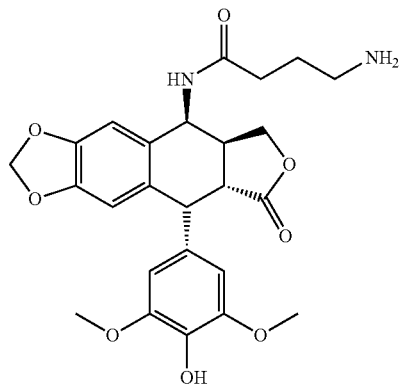

Compound 57: 5-Aminopentanoic acid N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-amide

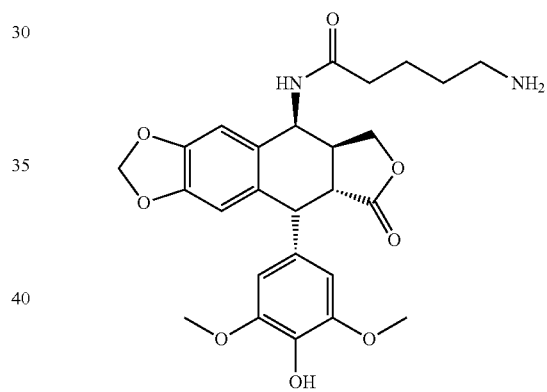

Compound 58: 3-(5-Aminopentylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide

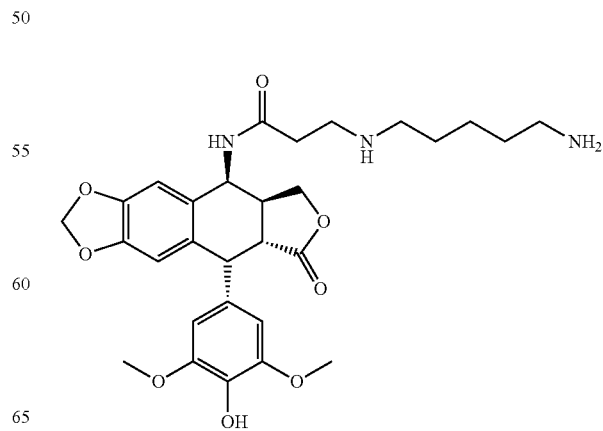

Urea Series:

Compound 39: 1-(4-Aminobutyl)-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea

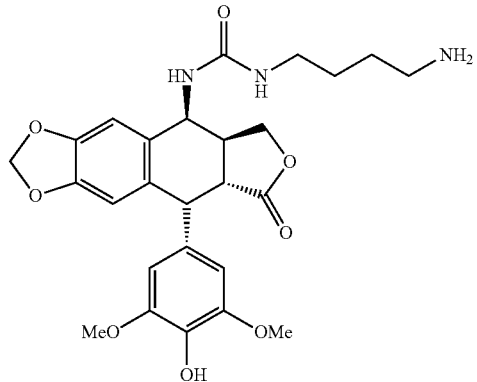

Compound 40: 1-[4-(3-Aminopropylamino)-butyl]-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea

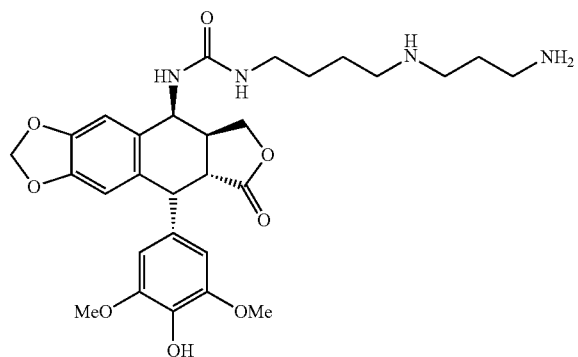

Compound 41: 1-[3-(4-Aminobutylamino)-propyl]-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea

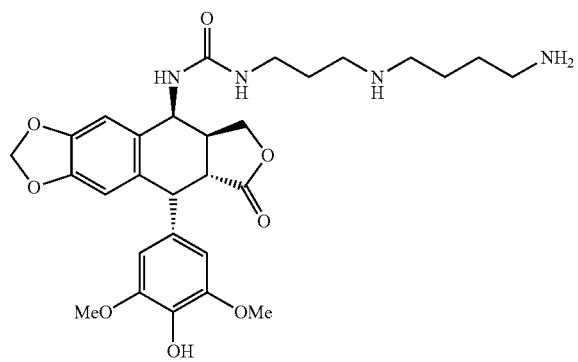

Compound 42: 1-[3-(3-Aminopropylamino)-propyl]-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea

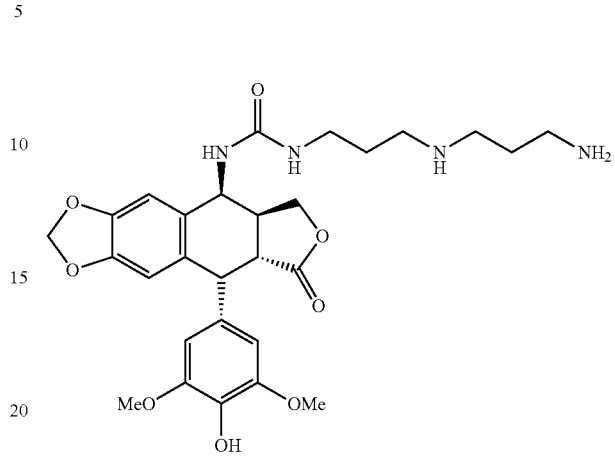

Compound 43: 1-[4-(4-Aminobutylamino)-butyl]-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea

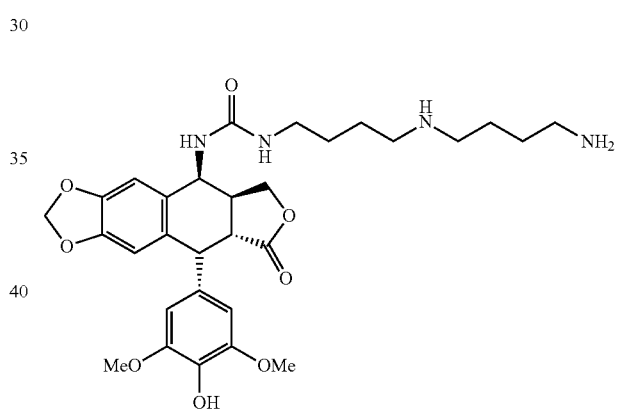

Compound 44: 1-{2-[3-(4-Aminobutylamino)-propylamino]-ethyl}-3-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-urea

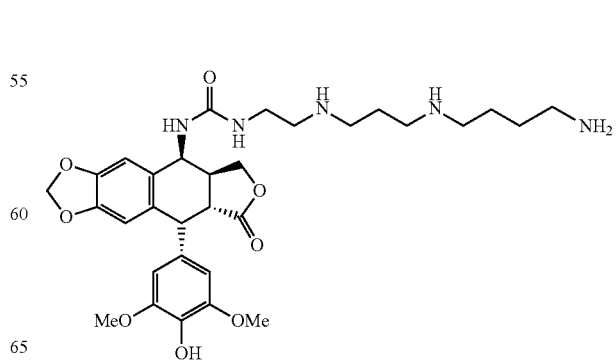

Compound 45: 1-{2-[4-(3-Aminopropylamino)-butylamino]-ethyl}-3-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-urea

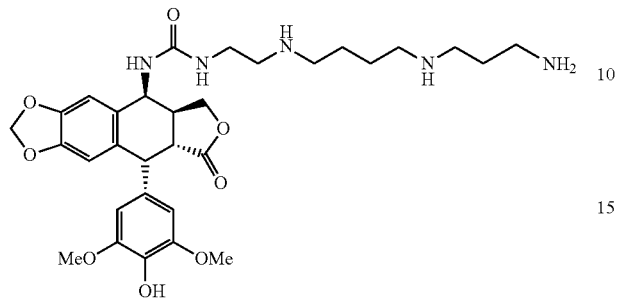

Compound 46: 1-{4-[4-(4-Aminobutylamino)-butylamino]-butyl}-3-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-urea

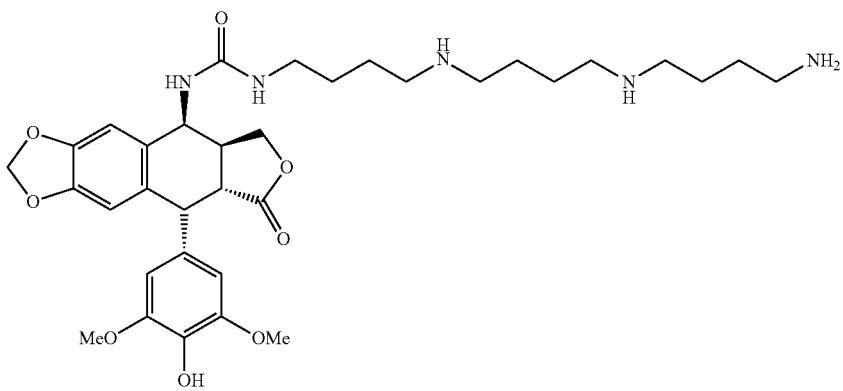

Compound 47: 1-{3-[3-(3-Aminopropylamino)-propylamino]-propyl}-3-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-urea

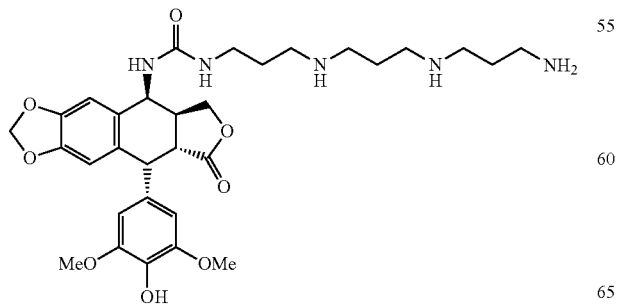

Compound 48: 1-{3-[4-(3-Aminopropylamino)-butylamino]-propyl}-3-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-urea

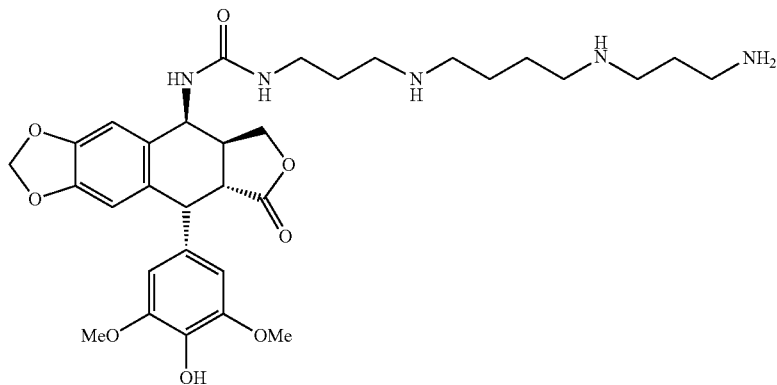

Compound 49: 1-[2-{3-[4-(3-Aminopropylamino)-butylamino]-propylamino}-ethyl]-3-[9-(4-hydroxy-3,5-dimethoxyphenyl)-8-oxo-5,5a,6,8,8a,9-hexahydrofuro-[3',4':6,7]naphtho[2,3-d][1,3]dioxol-5-yl]-urea

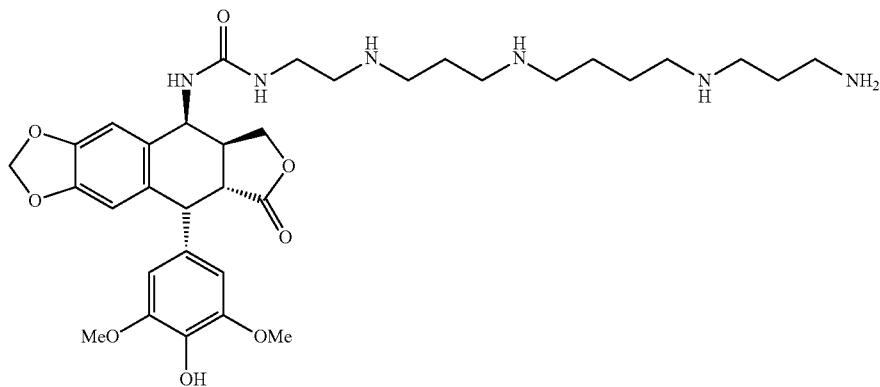

Compound 50: 1-[3-{3-[4-(3-Aminopropylamino)-butylamino]-propylamino}-propyl]-3-[9-(4-hydroxy-3,5-dimethoxyphenyl)-8-oxo-5,5a,6,8,8a,9-hexahydrofuro-[3',4':6,7]naphtho[2,3-d][1,3]dioxol-5-yl]-urea

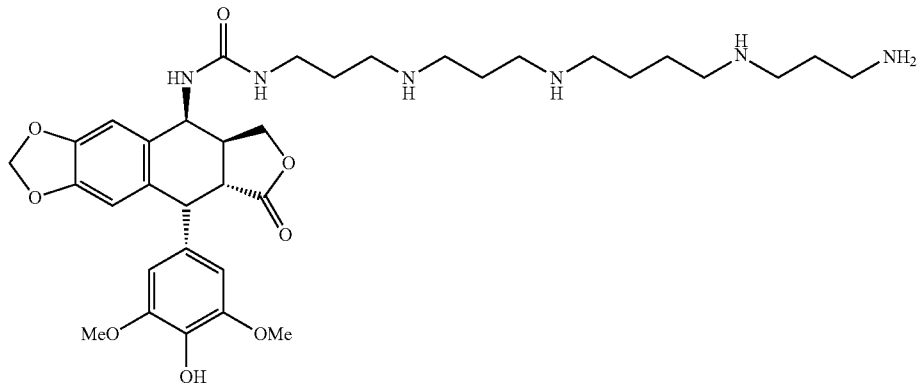

Compound 64: 1-[4-{3-[4-(3-Aminopropylamino)-butylamino]-propylamino}-butyl]-3-[9-(4-hydroxy-3,5-dimethoxyphenyl)-8-oxo-5,5a,6,8,8a,9-hexahydrofuro-[3',4':6,7]naphtho[2,3-d][1,3]dioxol-5-yl]-urea

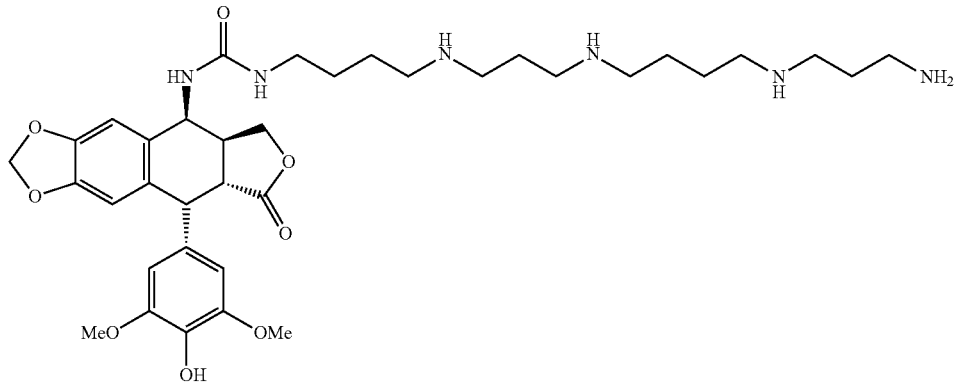

Compound 65: 1-(5-{3-[4-(3-Aminopropylamino)-butylamino]-propylamino}-pentyl)-3-[9-(4-hydroxy-3,5-dimethoxyphenyl)-8-oxo-5,5a,6,8,8a,9-hexahydrofuro-[3',4':6,7]naphtho[2,3-d][1,3]dioxol-5-yl]-urea

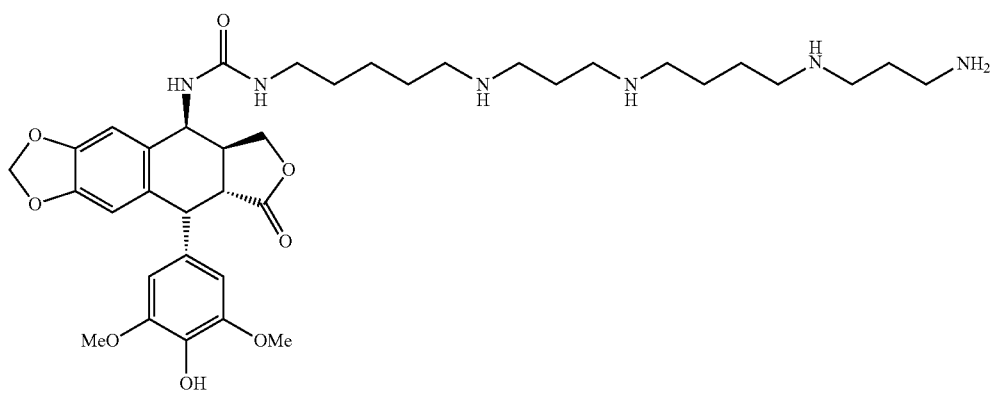

Compound 66: 1-{3-[3-(4-Aminobutylamino)-propylamino]-propyl}-3-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-urea

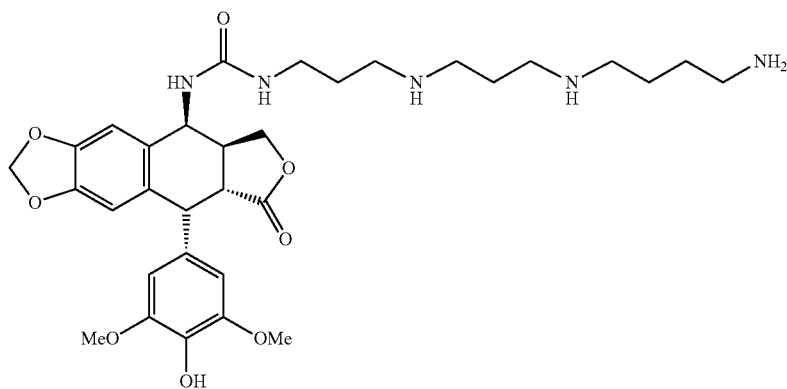

Compound 67: 1-{4-[3-(4-Aminobutylamino)-propylamino]-butyl}-3-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-urea

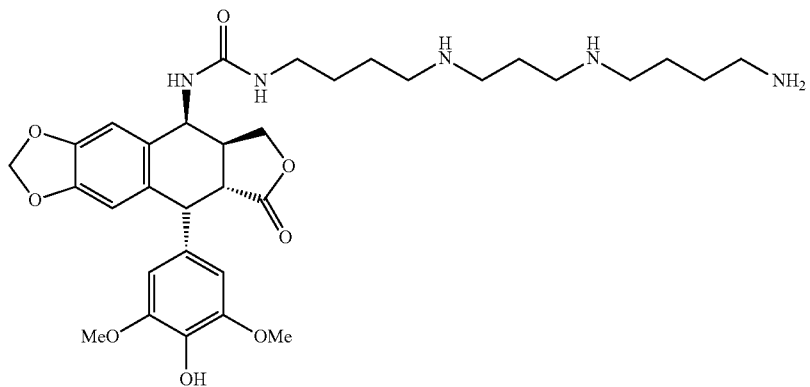

Compound 68: 1-{4-[4-(3-Aminopropylamino)-butylamino]-butyl}-3-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-urea

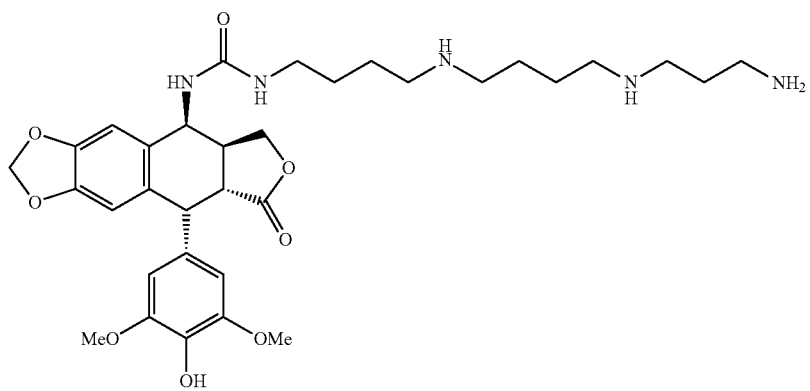

Sulfamido Series:

Compound 61: 2-(4-Aminopentylamino)-ethanesulfonic acid N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-amide Compound 62: 2-[4-(4-Aminobutylamino)-butylamino]-ethanesulfonic acid N-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-amide

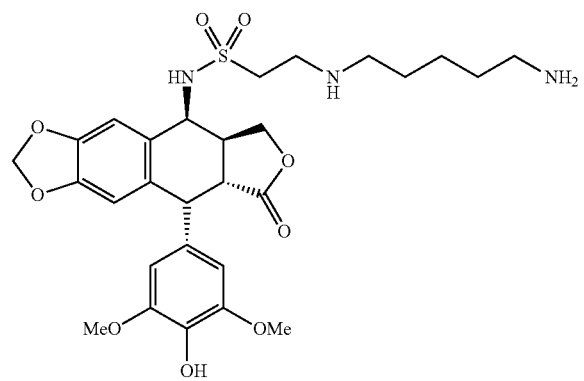

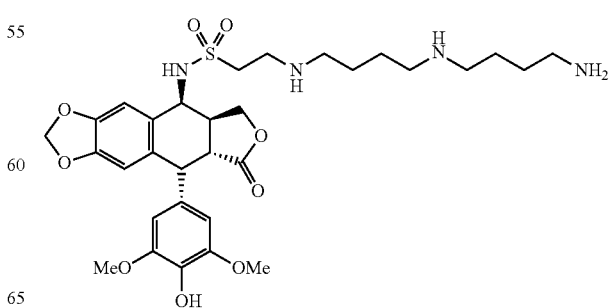

Compound 63: 2-[3-(3-Aminopropylamino)-propylamino]-ethanesulfonic acid N-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-amide Compound 52: 2-[3-(4-Aminobutylamino)-propylamino]-ethanesulfonic acid N-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-amide

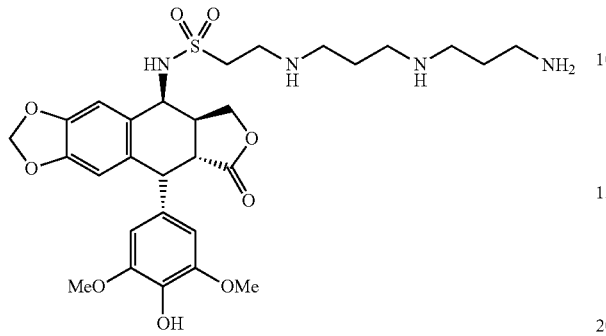

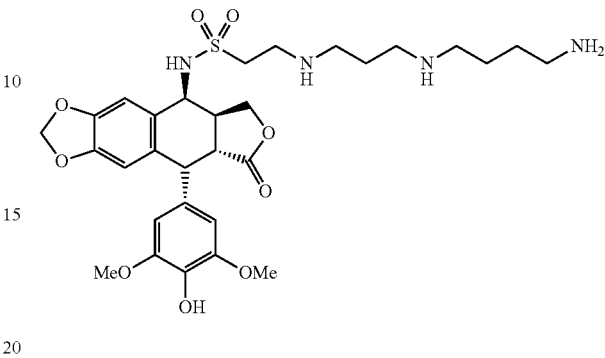

Compound 51: 2-(4-aminobutylamino)-ethanesulfonic acid N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-amide Compound 53: 2-[4-(3-Aminopropylamino)-butylamino]-ethanesulfonic acid N-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-amide

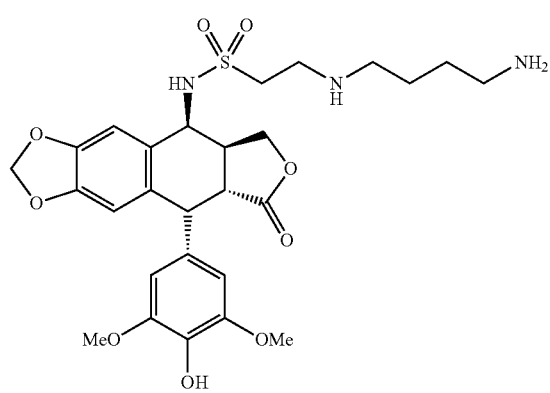

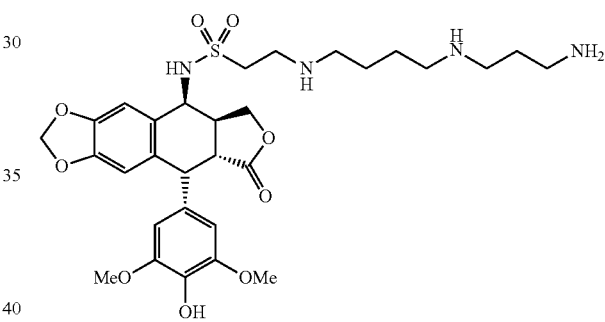

Compound 54: 2-{3-[4-(3-Aminopropylamino)-butylamino]-propylamino}-ethanesulfonic acid 3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-amide

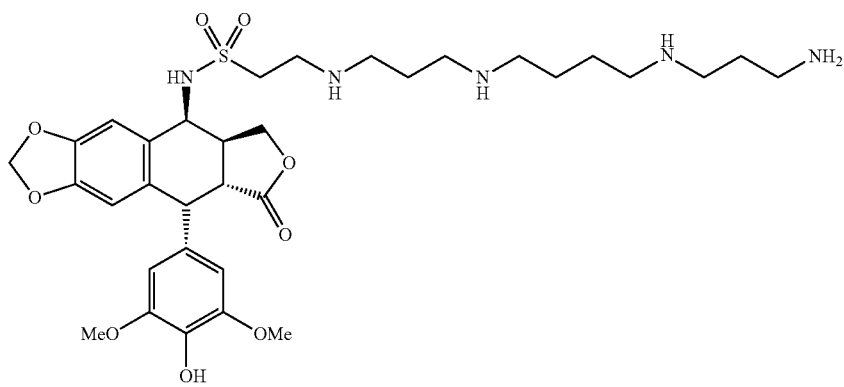

Compound 59: 2-{3-[3-(3-Aminopropylamino)-propylamino]-propylamino}-ethanesulfonic acid 3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-amide

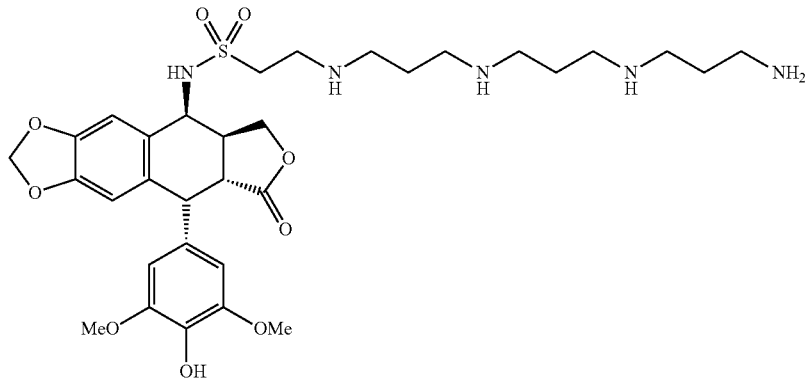

Compound 60: 2-{4-[4-(4-Aminobutylamino)-butylamino]-butylamino}-ethanesulfonic acid 3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-amide

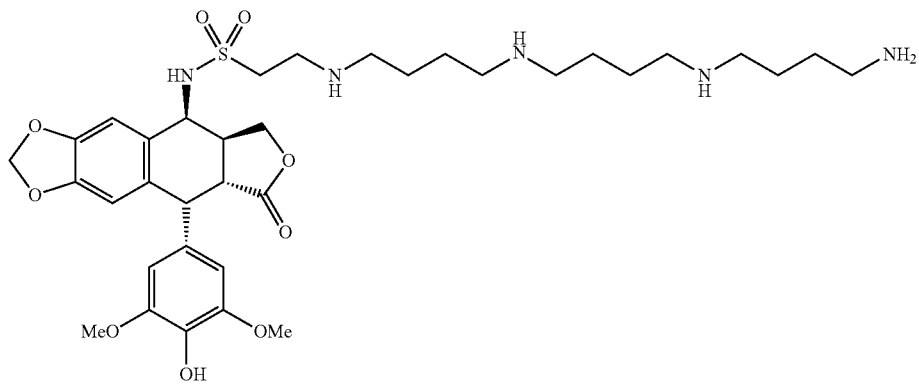

and inorganic or organic acid addition salts thereof.

The compounds of the invention are, for example, the compounds of the general formula 1 wherein:

R represents a hydrogen atom or $C_{1-4}$alkyl,

A represents $CO(CH_2)_n$, $CONH(CH_2)_n$, or $SO_2(CH_2)_n$ where n=2, 3, 4, or 5, R1 represents a hydrogen atom or $C_{1-4}$alkyl, R2 represents a hydrogen atom or $C_{1-4}$alkyl, or can also be $(CH_2)_m$—NR3R4, where m=2, 3, 4, or 5, R3 represents a hydrogen atom or $C_{1-4}$alkyl, R4 represents a hydrogen atom or $C_{1-4}$alkyl, or can also be $(CH_2)_p$—NR5R6, where p=2, 3, 4, or 5, R5 represents a hydrogen atom or $C_{1-4}$alkyl, and R6 represents a hydrogen atom or $C_{1-4}$alkyl, or can also be $(CH_2)_q$—$NH_2$, where q=2, 3, 4, or 5.

with the exception of compounds wherein $A=CO(CH_2)_2$ or $A=SO_2(CH_2)_3$ and R1=R2=H.

Advantageously, R1=H, R3=H, and R5=H. R can also represent preferably a hydrogen atom.

The compounds of the invention are, for example, compounds of the general formula 1 wherein A represents $CO(CH_2)_n$ or $CONH(CH_2)_n$ where n=2, 3, 4, or 5, with the exception of compounds wherein $A=CO(CH_2)_2$ and R1=R2=H.

The compounds of the invention are, for example, compounds of the general formula 1 such as defined above wherein R=H.

The compounds of the invention are, for example, compounds of the general formula 1, such as defined above, wherein R1 and R2 are not simultaneously H when R=H and $A=CO(CH_2)_n$ where n=2, 3, or 4.

One particular embodiment of the invention relates to compounds of the general formula 1, such as defined above, wherein $R2=(CH_2)_m$—NR3R4, preferably $R4=(CH_2)_p$—NR5R6, and in particular m=3 or 4, and p=3 or 4, for example compounds of the general formula 1, wherein R6=H, $C_{1-4}$alkyl, or else $(CH_2)_q$—$NH_2$, where q=3.

The present invention relates in particular to compounds of the formula 1 selected from the group consisting of compounds 1 to 50, 55 to 58, and 64 to 68 described hereabove, and inorganic or organic acid addition salts thereof.

More particularly, the compounds of the invention may be selected from the group consisting of compounds 14 to 50, and 64 to 68 such as defined above, and inorganic or organic acid addition salts thereof.

For example, the compounds of the invention can be selected from the group consisting of compounds 14, 16 to 18, 21 to 24, 27, 28, 31 to 36, 39 to 41, 44 to 50, 54, 64 to 68, such as defined above, and inorganic or organic acid addition salts thereof.

The isomeric compounds according to the invention are within the scope of the invention.

In the present invention, <<pharmaceutically acceptable>> as used herein means what is useful in the preparation of a pharmaceutical composition which is generally safe, non toxic and which is not biologically or otherwise undesirable, and which is convenient for both veterinary and human pharmaceutical use.

As used herein, the term <<pharmaceutically acceptable salts>> of a compound means salts which are pharmaceutically acceptable, as defined herein, and which have the desired pharmacological activity of the parent compound. Within the scope of the present invention, it is meant more particularly addition salts of pharmaceutically acceptable inorganic or organic acids.

Pharmaceutically acceptable acids include, but are not limited to, hydrochloric, hydrobromic, sulfuric, phosphoric, acetic, trifluoroacetic, lactic, pyruvic, malonic, succinic, glutaric, fumaric, tartaric, maleic, citric, ascorbic, oxalic, methanesulfonic, camphoric, and sulfamic acids. The compounds according to the invention are characterized in that they are water soluble by forming inorganic or organic salts, together with the basic nitrogen atoms of the side chain in the 4-position.

A further object of the present invention is the use of compounds of the formula 1, for anticancer treatment of liquid tumors and solid tumors, such as melanomas, colorectal cancers, lung cancers, prostate cancers, bladder cancers, breast cancers, uterus cancers, esophageal cancers, stomach cancers, pancreas cancers, liver cancers, ovarian cancers, leukemias in particular lymphomas and myelomas, ENT cancers and brain cancers.

These compounds can be used in combination with other anticancer treatments, which may be cytotoxic or cytostatic, such as platinum derivatives, taxans, vincas, 5-FU, to increase their therapeutic effectiveness for the purpose of treating tumors resistant to usual therapies.

Another object of the present invention is a process for preparing these compounds. This process involves the podophyllotoxin of the formula 2 as a raw material. In particular the demethylation reaction of the podophyllotoxin by the reactant pair methionine (or dimethylsulfide)-methanesulfonic acid, or in the presence of trifluoroacetic acid or acetone, and water, is used according to the method described in French patent FR 2 742 439, to yield the 4'-demethylepipodophyllotoxin of the formula 3. This compound can be subjected to a Ritter reaction in the presence of sulfuric acid or other strong acid, with an organic nitrile of the formula Ra—CN where Ra=—(CH$_2$)$_n$—X or —CH=CH$_2$, where n=3, 4, or 5 and X represents a halogen atom, such as a chlorine atom, to obtain a compound of the formula 4. The organic nitrile may be in particular chloroacetonitrile, or more generally a halogenoalkylonitrile of the formula NC—(CH$_2$)$_n$—X.

The intermediate amide of the formula 4a can thus be formed, wherein n is from 3 to 5. When acrylonitrile is reacted instead of halogenoakylonitriles, the vinylamide intermediate of the formula 4b is obtained.

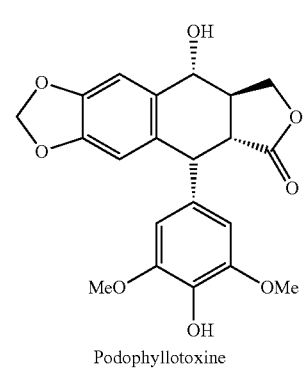

formula 2

Podophyllotoxine

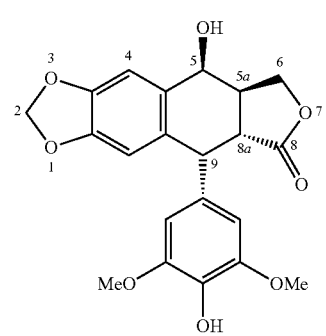

Formula 3

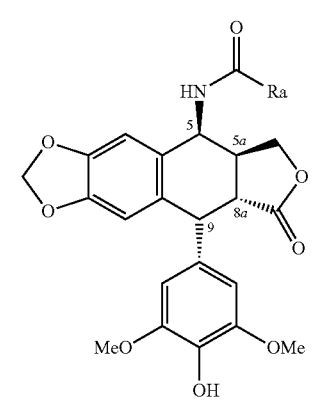

Formula 4

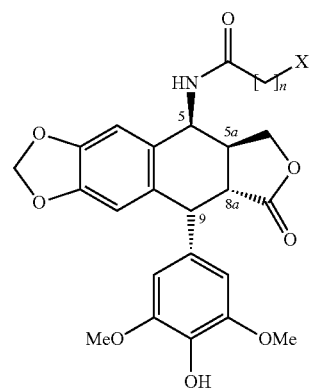

Formula 4a

Formula 4b

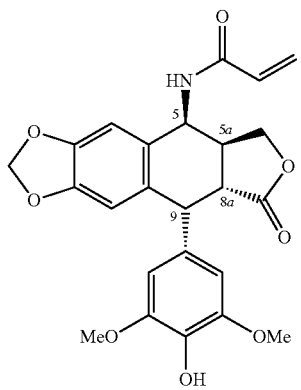

Formula 6

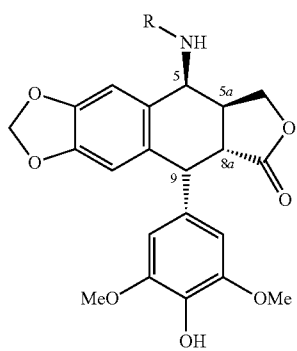

The amide intermediate of the formula 4a wherein n=1, and X=Cl, which is a known intermediate, is treated with thiourea in refluxing acetic acid to provide with an excellent yield the 4β-amino-4-deoxy-4'-demethylpodophyllotoxin, a compound of the formula 6 wherein R=H, according to the method described in patent application WO 2007/010007.

The amide compounds of the formula 1 wherein A=$(CH_2)_n$—X and R=H are prepared as follows:

The intermediates of the formula 4 (4a or 4b) can be subjected to an alkylation with an amine (monoamine, diamine or polyamine), in particular putrescine, spermidine, or spermine, in a protected form. Polyamines have several amine functions, so that they should be protected by protecting groups to leave a free primary amine position, for a good reaction selectivity. It is within the knowledge of the person skilled in the art to select protecting groups such as benzyloxycarbonyl, or t-butyloxycarbonyl groups to protect those amine functions which should be left unreacted.

For example, spermine protected by benzyloxycarbonyl (Z) or tertiary-butyloxycarbonyl (BOC) groups is described. Likewise spermidine protected by Z or BOC groups is described.

Thus, the alkylation reaction will be carried out between a compound of the formula 4 and an amine of the formula HNR1R2a in a protected form, wherein:

R1 is as defined above,
R2a=$C_{1-4}$alkyl, an amine-protecting group, or $(CH_2)_m$—NR3aR4a, where m is as defined above,
R3a=$C_{1-4}$alkyl, or an amine-protecting group,
R4a=$C_{1-4}$alkyl, an amine-protecting group, or $(CH_2)_p$—NR5aR6a, where p is as defined above,
R5a=$C_{1-4}$alkyl, or an amine-protecting group,
R6a=$C_{1-4}$alkyl, an amine-protecting group, or $(CH_2)_q$—NR7aR8a, where q is as defined above,
R7a=H or an amine-protecting group, and
R8a=an amine-protecting group.

Protecting amine functions is suitable to prevent the synthesis of undesirable by-products, such that there is only one reactivity site, during the coupling reaction.

The following publications disclose the preparation of the various amines with protecting groups: Protective Groups in Organic Synthesis (Th. W. Greene, $2^{nd}$ Ed, John Wiley and sons, 1991), or in Synthesis 2002, 15, 2195; Bull. Chem. Soc. Jpn. 1998, 71, 699; Tet. Let. 1998, 39, 439 and 443; Tet. Let. 2001, 42, 2709; OPPI 1994, 26, 599; Synthesis 1994, 37; J. Org. Chem. 1998, 63, 9723; Tet. Let. 1994, 35, 2057, and 2061, J. Med. Chem. 2004, 47, 6055; J. Med. Chem. 2003, 46, 5712; Tet. Let. 1995, 36, 9401; Tet. 2000, 56, 2449.

The amine-protecting groups may be in particular Z or BOC. Advantageously, all the protecting groups on the protected amine will be identical.

The alkylation reaction between the protected amine and the compound of the formula 4 produces a compound of the formula 5 followed by a compound of the formula 7a after deprotection of the amine functions protected by amine-protecting groups (when such groups are present).

Formula 5

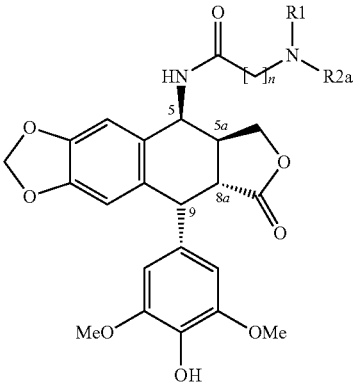

Formula 7

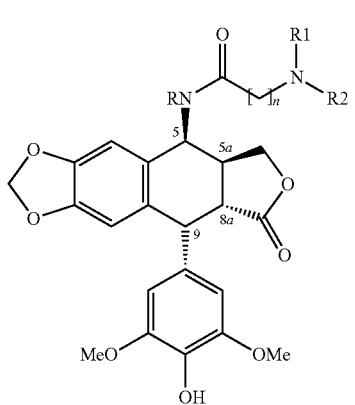

Formula 7a

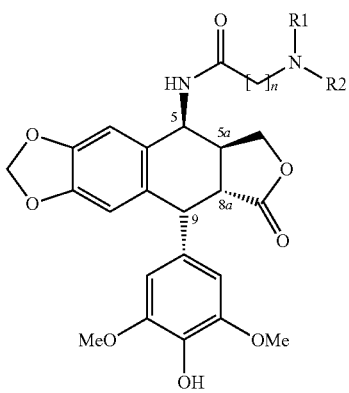

Thus, according to the set of selective protections by amine-protecting groups, for example BOC or Z, those skilled in the art can prepare the compounds of the formula 7a.

Optionally, the last step of the process according to the invention is the deprotection of the amine functions protected by appropriate groups.

The resulting compounds will then be isolated from the reaction mixture by techniques well known to those skilled in the art.

The compounds of the present invention contain chiral centers resulting from naturally occurring podophyllotoxin. In the compound of the formula 2 (4'-DMEP), the hydrogen atoms in the 5, 5a, 8a, and 9 positions have the following stereochemistry: H5α, H5aα, H8aβ, H9β. In the compound of the formula 3, the configuration of the asymmetric carbons is advantageously the following: 5S, 5aS, 8aR, 9R.

The urea compounds of the formula 10 are prepared from the 4β-chloroacetamido-4'-demethylpodophyllotoxin of the formula 4a (n=1, X=Cl), in which the 4'-phenol is protected with a hydroxyl-protecting group Y such as a benzyloxycarbonyl group. Treatment with the thiourea provides the amino compound of the formula 8 with R=H, wherein the group in the 4'-position is protected with a protecting group Y such as a group Z (benzyloxycarbonyl), wherein the compounds of the formula 8 with R≠H can be formed according to a process disclosed in U.S. Pat. No. 7,378,419.

Formula 8

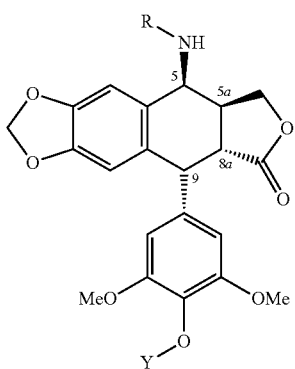

Formula 9

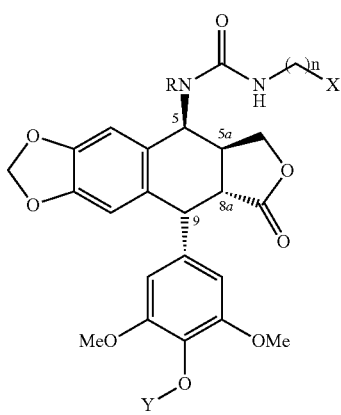

Formula 10a

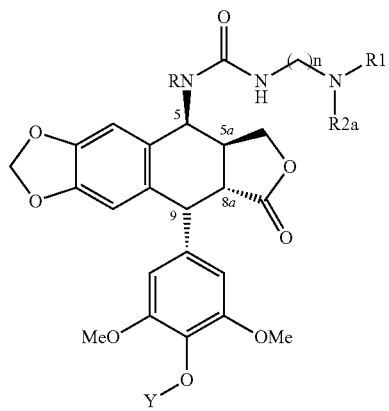

Formula 10b

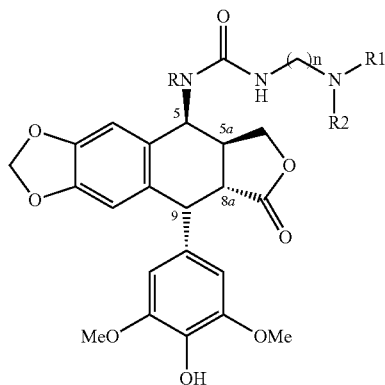

Formula 10c

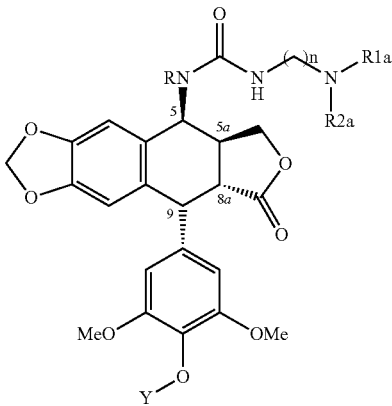

Formula 11

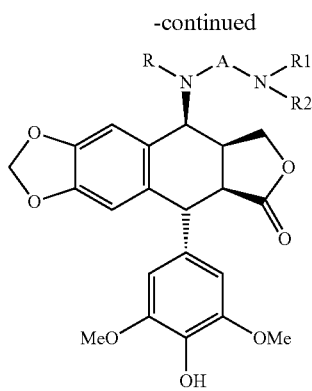

This compound of the formula 8 (in particular wherein R=H) is then reacted with isocyanates, such as halogenoalkylisocyanates of the formula O=C=N—(CH$_2$)$_n$—X, wherein X represents a halogen and n is a chain having from 2 to 5 CH$_2$, to provide the compounds of the formula 9 (according to the procedure disclosed in *Heterocycles* 1994, 39, 361). This intermediate of the formula 9 is reacted with the protected mono, di, tri, or tetramines (of the formula HNR1R2a) as mentioned above under traditional alkylation conditions, i.e. in particular at room temperature in DMF in the presence of triethylamine and KI, to provide compounds of the formula 10a, followed by compounds of the formula 10b after deprotection of the 4'-position on the podophyllotoxin backbone and of the protected amine functions.

The resulting compounds will then be isolated from the reaction mixture by techniques well known to those skilled in the art.

The ureas can also be prepared with the compound of the formula 8 (in particular wherein R=H), and phosgene or triphosgene to provide a non-isolated, activated carbonylated intermediate. This intermediate corresponds to the following formula:

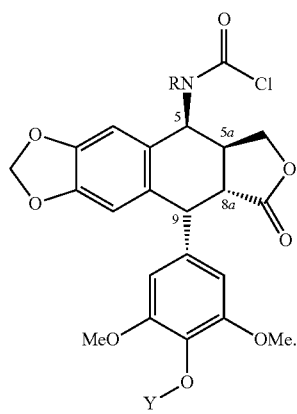

This intermediate is further reacted directly with a protected amine, diamine or polyamine of the formula H$_2$N—(CH$_2$)$_n$—NR1aR2a, wherein R1a represents H, C$_{1-4}$alkyl or an amine-protecting group, and wherein R2a and n are as defined above (where R1a≠H when R2a=C$_{1-4}$alkyl or (CH$_2$)$_m$—NR3aR4a) to obtain a compound of the formula 10c, with the remaining synthesis being performed as described above (deprotection of the amine functions and of the phenol). The last deprotection stage, either in an acid medium, in the case of the group BOC, or by catalytic hydrogenation in the case of the group Z, leads then to the free polyamine compound of the general formula 1 wherein A=CONH(CH$_2$)$_n$.

However, polyamine alkylation performed on podophyllotoxin halogenoalkylamides is not a univocal reaction. The processing conditions of this classically used alkylation are an alkaline medium. It is important to conduct the reaction in a weakly alkaline medium, such as in the presence of triethylamine. The alkalinity of the medium can lead according to the procedure to a by-product resulting from the epimerization of the proton in the 2-position thus providing the cis-lactone derivative, of the formula 11, i.e. the isomer of the formula 1. A precise chromatography makes it possible however to isolate the desired trans-lactone derivative. The following examples show an alternative method to prevent such possible epimerization. This is by forming an alkanoic acid chain on the protected polyamine (compound of the formula 12 wherein R1a is as defined above), followed by coupling the resulting product through peptide coupling with the 4β-amino-4-deoxy-4'-demethylpodophyllotoxin of the formula 6 (in particular wherein R=H), according to the reaction scheme below:

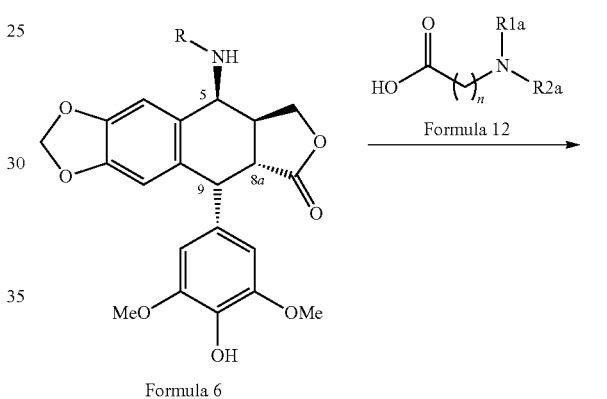

Formula 6

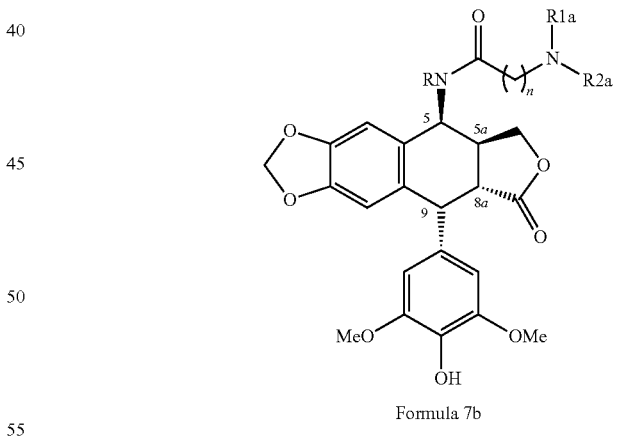

Formula 7b

This peptide coupling is performed, advantageously in the presence of TBTU, preferably with a polyamine protected with benzyloxycarbonyl groups, and having a propionic, butyric, or pentanoic moiety. The acid intermediates having a moiety with 2 carbons (formula 12, n=2) are prepared by condensation with methyl acrylate in a similar way to the products described in *Tet.* 2006, 62, 8332. The acid intermediates of the formula 12 wherein n=3 to 5 are prepared by an ordinary alkylation of the halogenoalkylester-protected amine which is then saponified into carboxylic acid. The compounds of the formula 7b are subsequently obtained to provide the compounds of the formula 7 after deprotection of the protected amine functions.

The resulting compounds will then be isolated from the reaction mixture by techniques well known to those skilled in the art.

The sulfonamide compounds are prepared as follows:

The compound of the formula 8 (in particular wherein R=H) is reacted with chloroethyl sulfonyl chloride, to obtain the vinylsulfonamide intermediate, which is opposite to the various protected polyamines. The deprotections are performed by a traditional hydrogenolysis in the presence of palladium on carbon, in the case of a protecting group Z, or in an acid medium in the case of the protecting group BOC.

The following non limiting examples illustrate the process techniques used:

1—Preparation of Intermediates

Intermediate I:
4-amino-4'-demethyl-4-deoxypodophyllotoxin
(Formula 6 wherein R=H)

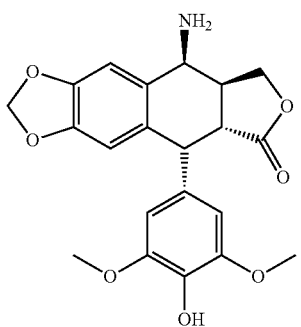

This compound is prepared as described in patent application WO 2007/010007.

Stage 1: Ritter reaction: Preparation of 4β-chloroacetamido-4'-demethyl-4-deoxypodophyllotoxin of the formula 4a (wherein n=1 and X=Cl)

To a suspension of 30 g (0.075 mol) of 4'-demethylepipodophyllotoxin of the formula 3 in 47.5 mL (0.75 mol) of chloroacetonitrile, 0.5 mL of concentrated sulfuric acid is added dropwise at room temperature. The mixture is left under stirring at this temperature for 1 hour during which period dissolution is observed followed with reprecipitation. 300 mL of 2-propanol are added. The precipitate is filtered, rinsed with 200 mL of 2-propanol and water up to pH=7. The resulting white solid is dried under vacuum at 40° C. to obtain 32.9 g of the chloroacetamido compound of the formula 4a (n=1, X=Cl), i.e. 93% yield. Mp=240° C.

Stage 2: Preparation of
4-amino-4'-demethyl-4-deoxypodophyllotoxin
(formula 6 wherein R=H)

A suspension of 17 g (0.0358 mol) of the 4β-chloroacetamido-4'-demethyl-4-deoxypodophyllotoxin obtained above in 75 mL of glacial acetic acid is heated to 80° C. with stirring. 4.2 g (0.0537 mol) of thiourea is added in one portion. The mixture is left under stirring at this temperature for 1 h 30, during which period dissolution is observed followed with reprecipitation. The reaction mixture is filtered hot, rinsed with 75 mL of glacial acetic acid and diisopropyl ether. The resulting white solid is dried under vacuum at 40° C. to obtain 14.6 g of the compound of the formula 6, in hydrochloride form corresponding to a 93% molar yield. Mp >260° C.
$^1$H-NMR (DMSO) δ 8.63 (m, 2H), 8.32 (m, 1H), 7.23 (s, 1H, $H_8$), 6.60 (s, 1H, $H_8$), 6.18 (s, 2H, $H_{2'}$, $H_{6'}$), 6.05 (d, 2H, J=2.1 Hz, OCH$_2$O), 4.73 (d, 1H, J=4.5 Hz, $H_4$), 4.56 (d, 1H, J=5.2 Hz, $H_1$), 4.34 (m, 2H, $H_{11a}$ and $H_{11b}$), 3.65 (dd, 1H, J=5.2 Hz, $H_2$), 3.62 (s, 6H, 2×OCH$_3$), 3.06 (m, 1H, $H_3$).

Intermediate II: Preparation of 4β-acrylamido-4'-demethyl-4-deoxypodophyllotoxin

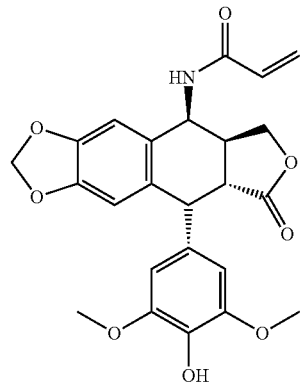

Formula 5

To a suspension of 3 g (0.0075 mol) of 4'-demethylepipodophyllotoxin of the formula 3 in 10 mL of acrylonitrile, a few drops of concentrated sulfuric acid are added at room temperature. The mixture is left under stirring at this temperature for 3 hours during which period dissolution is observed followed with reprecipitation. 50 mL of 2-propanol are added. The precipitate is filtered, rinsed with 2-propanol and water up to pH=7. The resulting white solid is dried under vacuum at 40° C. to obtain 2.64 g of the acrylamide compound. Mp=180° C. TLC SiO$_2$ (30:70 heptane:AcOEt) Rf 0.25. Anal. C$_{24}$H$_{23}$NO$_3$, H$_2$O (MW=471.464): calc. C % 61.14, H % 5.63, N % 2.66. found: C % 60.84, H % 5.34, N % 2.97.

Intermediate III: Preparation of 4β-chlorobutyramido-4'-demethyl-4-deoxypodophyllotoxin

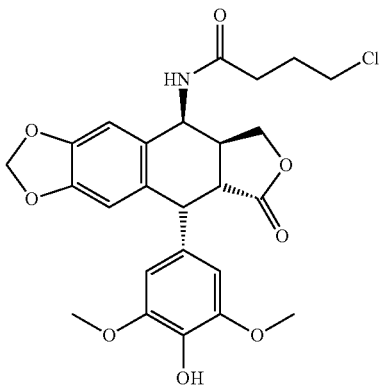

Stage 1: Preparation of 4β-chlorobutyramido-4-deoxypodophyllotoxin

This compound is prepared from podophyllotoxin and 4-chlorobutyronitrile according to the procedure disclosed in stage 1 of the preparation of intermediate I, for the reaction of chloroacetonitrile with 4'-demethylepipodophyllotoxin. TLC SiO$_2$ (9:1 CH$_2$Cl$_2$:Acetone) Rf=0.38, Yield=71%.

Stage 2: Preparation of 4β-chlorobutyramido-4'-demethyl-4-deoxypodophyllotoxin (formula 4a wherein n=3 and X=Cl))

4.46 g of the compound obtained in stage 1 above are suspended with stirring in 21.16 mL of methane sulfonic acid. 1.93 g of D,L-methionine is then added and the stirring is maintained for 2 hrs. The reaction mixture is poured into water with stirring and a precipitate is formed. Filtration and washing with water until neutral give, after drying and dewatering, 2.26 g (Yield=52%) of demethylation product. TLC SiO$_2$ (9:1 CH$_2$Cl$_2$:Acetone) Rf=0.20. The product is used directly without purification in the following alkylation steps.

Intermediate IV: Preparation of 4β-bromopentanamido-4'-demethyl-4-deoxypodophyllotoxin This compound is prepared in a similar way to the 4β-chloroacetamido-4'-demethyl-4-deoxypodophyllotoxin, stage 1 of intermediate I, but with the use of the corresponding reactant, i.e. 5-bromobutyronitrile. 4β-Bromopentanamido-4'-demethyl-4-deoxypodophyllotoxin is obtained with 57% yield. TLC SiO$_2$ (95:5 CH$_2$Cl$_2$:MeOH) Rf 0.28. Spectrum characteristic signals $^1$H-NMR (DMSO) δ 5.39 (t, 2H, J=6.4 Hz, CH$_2$Br), 2.17 (t, 2H, J=7.2 Hz, CH$_2$CO), 1.79 (m, 2H, CH$_2$), 1.66 (m, 2H, CH$_2$).

2—Preparation of Compounds of the Invention

Example 1

Preparation of 3-dimethylamino-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide or (4β-dimethylaminopropionamido)-4'-demethyl-4-deoxypodophyllotoxin) (Compound 5)

500 mg of 4β-amino-4'-demethyl-4-deoxypodophyllotoxin of the formula 6, and 146 mg of 3-dimethylaminopropionic acid are dissolved in 50 mL of acetonitrile, together with 0.21 mL of triethylamine with stirring. 400 mg of TBTU are added and stirring is continued for 6 h at room temperature. The reaction mixture is poured into water (300 mL) and extracted with ethyl acetate (3×100 mL). The organic phases are dried over Na$_2$SO$_4$, filtered and evaporated. The residue is flash chromatographed on SiO$_2$ (elution with 78:20:2 CH$_2$Cl$_2$:MeOH:NH$_4$OH). After evaporation, the residue is again chromatographed on preparative HPLC (X Bridge OBD C18, 30×250 mm, 10μ) gradient elution CH$_3$CN/HCl 5 mM (from 10/90 to 80/20). The fractions are extracted with ethyl acetate (2×100 mL), dried, and evaporated. The residue is salified with HCl isopropanol in ethyl ether, filtered and dried to provide 246 mg of hydrochloride, as a white powder. Yield=37%. TLC SiO$_2$ (90:9:1 CH$_2$Cl$_2$:MeOH:NH$_4$OH) Rf 0.38. NMR of the base: $^1$H-NMR (DMSO) δ 8.36 (d, 1H, NH), 8.28 (s, 1H, OH), 6.76 (s, 1H, H$_5$), 6.53 (s, 1H, H$_8$), 6.24 (s, 2H, H$_{2'}$, H$_{6'}$), 5.99 (d, 2H, J=8.4 Hz, OCH$_2$O), 5.16 (dd, 1H, H$_4$), 4.50 (d, 1H, J=5 Hz, H$_1$), 4.25 (t, 1H, H$_{11a}$), 3.87 (t, 1H, H$_{11b}$), 3.62 (s, 6H, OMe), 3.11 (dd, 1H, H$_2$), 2.93 (m, 1H, H$_3$), 2.42-2.55 (m, 2H, CH$_2$N), 2.24-2.33 (m, 2H, CH$_2$N), 2.12 (s, 6H, NMe$_2$). Mass spectrum (APCI), m/z=499, M-H+.

Example 2

Preparation of 4-dimethylamino-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide or (4β-dimethylaminobutyramido)-4'-demethyl-4-desoxypodophyllotoxin) (Compound 6)

A solution of 570 mg of intermediate III obtained above is stirred for 12 hrs in 25 mL of acetonitrile, together with 0.28 mL (5 eq.) of dimethylamine. The reaction mixture is then poured onto ice and a 1N HCl solution is added to pH=4. Extraction is carried out with methylene chloride and then the aqueous phase is alkalinized with a NaHCO$_3$ solution to pH=8. This phase is re-extracted with CH$_2$Cl$_2$, dried over Na$_2$SO$_4$, filtered and evaporated to yield 100 mg of an orange foam. The hydrochloride is formed in methylethylcetone, by adding an HCl isopropanol solution (3N). The hydrochloride is then filtered, washed with methylethylketone, followed with ethyl ether. Once dried, the crystals obtained represent 90 mg of an off-white powder. TLC SiO$_2$ (90:10:1 CH$_2$Cl$_2$:MeOH:NH$_4$OH) Rf 0.47. Mp=169° C. $^1$H-NMR (DMSO) δ 8.35 (d, 1H, NH), 6.75 (s, 1H, H$_5$), 6.51 (s, 1H, H$_8$), 6.20 (s, 2H, H$_{2'}$, H$_{6'}$), 5.96 (d, 2H, J=6.36 Hz, OCH$_2$O), 5.15 (dd, 1H, H$_4$), 4.47 (d, 1H, J=5 Hz, H$_1$), 4.26 (t, 1H, H$_{11a}$), 3.68 (t, 1H, H$_{11b}$), 3.59 (s, 6H, OMe), 3.34 (m, 2H, CH$_2$N), 3.08 (dd, 1H, H$_2$), 2.93 (m, 1H, H$_3$), 2.72 (s, 6H, NMe$_2$), 2.22 (m, 2H, CH$_2$CO), 1.86 (m, 2H, CH$_2$). Anal. C$_{27}$H$_{33}$ClN$_2$O$_8$, calc. C % 55.43; H % 6.37; N % 6.06; found C % 55.74, H % 6.01, N % 4.68.

Example 3

Preparation of 3-[(2-dimethylaminoethyl)-methylamino]-N-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-propionamide or (4β[-3-[2-(N-methyl-N,N-dimethylamino-2-ethyl)]propionamide)]-4'-demethyl-4-desoxypodophyllotoxin) (Compound 3)

200 mg of intermediate II are dissolved in 20 mL of THF, and 1.15 mL of N,N,N'-trimethylethylenediamine are introduced dropwise into the reaction mixture. The mixture is stirred for 12 h at room temperature, and then evaporated to dryness. At this stage a mixture of the 2 epimers in the 2-position (cis-lactone and trans-lactone) is obtained. A flash chromatography (elution with $CH_2Cl_2$:MeOH:$NH_4OH$ 90:10-0.5) affords 70 mg of the 2-epimerized derivative (cis-lactone). Mp=178° C. $^1$H-NMR (DMSO) δ 8.41 (d, 1H, J=8.96 Hz, CONH), 8.29 (m, 1H, OH), 6.95 (s, 1H, $H_8$), 6.89 (s, 1H, $H_5$), 6.42 (s, 2H, $H_{2'}$, $H_{6'}$), 6.01 (d, 2H, J=4.04 Hz, $OCH_2O$), 5.08 (dd, 1H, J=6.6 Hz, $H_4$), 4.37 (s, 1H, $H_1$), 4.28 (t, 1H, J=9.2 Hz, $H_{11a}$), 4.01 (dd, 1H, J=4 Hz, J'=9.6, $H_{11b}$), 3.79 (dd, 1H, J=1.6 Hz, J'=10.8, $H_2$), 3.69 (s, 6H, OMe), 3.32 (m, 3H, $H_3$, $COCH_2$), 2.63-2.27 (m, 6H, $CH_2N$), 2.194 (s, 3H, NMe), 2.101 (s, 6H, $NMe_2$).

Example 4

Preparation of 5-dimethylaminopentanoic acid N-[9-(4-hydroxy-3,5-dimethoxyphenyl)-8-oxo-5,5a,6,8,8a,9-hexahydrofuro[3',4':6,7]naphtho[2,3-d][1,3]-dioxol-5-yl]-amide or (4β-dimethylaminopentanamido-4'-demethyl-4-deoxypodophyllotoxin) (Compound 7)

700 mg of brominated intermediate IV obtained above are stirred in 3.3 mL of a 2M dimethylamine solution in THF, for 4 days, under nitrogen atmosphere. The medium is poured into ice and added with an HCl solution (0.1N) to pH=7. The medium is extracted with ethyl acetate to provide after drying over $Na_2SO_4$, filtration, and evaporation 341 mg of an oil which is then purified by flash chromatography on $SiO_2$ (97:7:0.7 $CH_2Cl_2$:MeOH:$NH_4OH$) to provide 200 mg of pure oil. The hydrochloride is formed by adding to the base dissolved in isopropanol a solution of hydrochloric ethanol to acidic pH. TLC $SiO_2$ (90:10:1 $CH_2Cl_2$:MeOH:$NH_4OH$) Rf 0.23. Mp tacky=224° C. $^1$H-NMR (DMSO) δ 8.38 (d, 1H, J=8.56 Hz, NH), 6.77 (s, 1H, $H_5$), 6.53 (s, 1H, $H_8$), 6.23 (s, 2H, $H_{2'}$, $H_{6'}$), 5.99 (d, 2H, J=12.4 Hz, $OCH_2O$), 5.18 (dd, 1H, J=8.16 Hz, J'=4.76 Hz, $H_4$), 4.49 (d, 1H, J=5.12 Hz, $H_1$), 4.29 (t, 1H, J=8 Hz, $H_{11a}$), 3.73 (t, 1H, J=10.34 Hz, $H_{11b}$), 3.63 (s, 6H, OMe), 3.22 (dd, 1H, J=5.16 Hz, J'=14.3 Hz, $H_2$), 3.3 (t, 2H, J=7.08 Hz, $CH_2N$), 2.93 (m, 1H, $H_3$), 2.71 (s, 6H, $NMe_2$), 2.20 (t, 2H, J=6.88 Hz, $CH_2CO$), 1.59 (m, 4H, $CH_2$).

Example 5

Preparation of 5-[(2-dimethylaminoethyl)-methylamino]pentanoic acid N-[9-(4-hydroxy-3,5-dimethoxyphenyl)-8-oxo-5,5a,6,8,8a,9-hexahydrofuro-[3',4':6,7]naphtho[2,3-d][1,3]dioxol-5-yl]-amide or 4β[5-[2-(N-methyl-N-dimethylamino-2-ethyl)]pentanamide)]-4'-demethyl-4-deoxypodophyllotoxin (Compound 55)

This compound is prepared in the same way as the compound of Example 2, but using the brominated intermediate IV and N,N,N'-trimethylethylenediamine. The 4β[5-[2-(N-methyl-N-dimethylamino-2-ethyl)]pentanamide)]-4'-demethyl-4-deoxy-podophyllotoxin contaminated with its 8a-epimer is obtained. A flash chromatography (eluting with $CH_2Cl_2$:MeOH:$NH_4OH$, 95:5:0.5 followed by 90:10-0.6) affords to isolate the title compound. The dihydrochloride is crystallized from isopropanol by adding hydrochloric ethanol. HPLC C8 Symmetry (Elution with 80 $KH_2PO_4$ Buffer at 3.4 g/L brought to pH=4 by addition of $H_3PO_4$/20 $CH_3CN$). Retention time: 4.95 min. $^1$H-NMR (DMSO) δ 8.38 (d, 1H, J=8.56 Hz, NH), 6.78 (s, 1H, $H_5$), 6.53 (s, 1H, $H_8$), 6.24 (s, 2H, $H_{2'}$, $H_{6'}$), 6.00 (d, 2H, J=11.3 Hz, $OCH_2O$), 5.19 (dd, 1H, J=8.15 Hz, J'=4.6 Hz, $H_4$), 4.50 (d, 1H, J=4.8 Hz, $H_1$), 4.29 (t, 1H, J=8 Hz, $H_{11a}$), 3.72 (dd, 1H, $H_{11b}$), 3.63 (s, 6H, OMe), 3.53 (m, 2H, $CH_2N$), 3.08-3.24 (m, 5H, $CH_2N$, $H_2$), 2.93 (m, 1H, $H_3$), 2.84 (s, 6H, $NMe_2$), 2.79 (s, 3H, NMe), 2.20 (t, 2H, J=6.88 Hz, $CH_2CO$), 1.69 (t, 2H, $CH_2$), 1.57 (m, 2H, $CH_2$).

Example 6

Preparation of 4-amino-N-[9-(4-hydroxy-3,5-dimethoxyphenyl)-8-oxo-5,5a,6,8,8a,9-hexahydro-furo[3',4':6,7]naphtho[2,3-d][1,3]dioxol-5-yl]-butyramide or (4β-aminobutanamido-4'-demethyl-4-deoxypodophyllotoxin) (Compound 56)

Stage 1:
To a solution of 1 g of 4β-amino-4'-demethyl-4-deoxy-podophyllotoxin of the formula 6 in 50 mL of acetonitrile are added 510 mg of 4-t-butoxycarbonylamino butyric acid (*Bioorg. Med. Chem. Lett.* 2005, 15, 1969) with stirring, together with 0.40 mL of triethylamine. 800 mg of TBTU are then added and stirring is continued at room temperature for 5 hrs. The reaction mixture is poured into water, and extracted with ethyl acetate. After evaporation of the solvent, the residue is purified by flash chromatography on $SiO_2$ (gradient elution from pure $CH_2Cl_2$ to 90:9:1 $CH_2Cl_2$:MeOH:$NH_4OH$). Preparative chromatography on X Bridge C18, OBD, 30×250 mm, 10μ, eluent: gradient from 10:90 $CH_3CN$/$H_2O$ to 90:10 $CH_3CN$/$H_2O$, provides after evaporation of the pure fractions 460 mg of a colorless oil. Yield=31%. TLC $SiO_2$ (90:9:1 $CH_2Cl_2$:MeOH:$NH_4OH$) Rf 0.20, $^1$H-NMR (DMSO) δ 8.25 (s, 1H, OH), 8.22 (d, 1H, J=8 Hz, NH amide), 6.79 (m, 1H, NH carbamate), 6.76 (s, 1H, $H_5$), 6.52 (s, 1H, $H_8$), 6.24 (s, 2H, $H_{2'}$, $H_{6'}$), 6.00 (d, 2H, J=13.2 Hz, $OCH_2O$), 5.17 (dd, 1H, J=8 Hz, J'=4.4 Hz, $H_4$), 4.49 (d, 1H, J=4.8 Hz, $H_1$), 4.27 (t, 1H, J=8 Hz, $H_{11a}$), 3.74 (t, 1H, J=9.6 Hz, $H_{11b}$), 3.62 (s, 6H, OMe), 3.15 (dd, 1H, J=14.4 Hz and J'=5.2 Hz, H2), 2.89-2.96 (m, 3H, $H_3$ and $CH_2N$), 2.13 (t, 2H, J=7.2 Hz, $CH_2CO$), 1.62 (m, 2H, CH2), 1.36 (s, 9H, t-Bu).

Stage 2:
The carbamate intermediate obtained in stage 1 above is stirred at room temperature for 4 h in 25 mL of $CH_2Cl_2$, in the presence of 25 mL of HCl isopropanol (3.3 M). After evaporation, a white precipitate is obtained, which is then filtered and washed with ethyl ether, and dried to yield 275 mg of hydrochloride as a white powder. Yield 67%. Mp=284° C. TLC $SiO_2$ (90:9:1 $CH_2Cl_2$:MeOH:$NH_4OH$) Rf 0.18, MS (ESI+) m/z=485 (M-H+). $^1$H-NMR (DMSO) δ 8.44 (d, 1H, J=7.6 Hz, NH amide), 8.27 (m, 1H, OH), 7.91 (m, 2H, $NH_2$ and HCl), 6.77 (s, 1H, $H_5$), 6.53 (s, 1H, $H_8$), 6.24 (s, 2H, $H_{2'}$, $H_{6'}$), 6.00 (d, 2H, J=11.6 Hz, $OCH_2O$), 5.19 (d, 1H, J=4.4 Hz, $H_4$), 4.52 (d, 1H, J=5.2 Hz, $H_1$), 4.31 (t, 1H, J=8 Hz, $H_{11a}$), 3.74 (m, 1H, $H_{11b}$), 3.63 (s, 6H, OMe), 3.17 (dd, 1H, J=14 Hz and J'=4.8 Hz, $H_2$), 2.95 (m, 1H, $H_3$), 2.81 (t, 2H, J=7.6 Hz, $CH_2N$), 2.27 (t, 2H, J=7.2 Hz, $CH_2CO$), 1.83 (m, 2H, $CH_2$).

Example 7

Preparation of 5-aminopentanoic acid N-[9-(4-hydroxy-3,5-dimethoxyphenyl)-8-oxo-5,5a,6,8,8a,9-hexahydrofuro[3',4':6,7]naphtho[2,3-d][1,3]-dioxol-5-yl]-amide or (4β-aminopentanamido-4'-demethyl-4-deoxypodophyllotoxin) (Compound 57)

This compound is prepared in the same way as in Example 6 above, but using 5-t-butoxycarbonylaminopentanoic acid.

Example 8

In the same way as in Example 6, but by using in place of 4-t-butoxycarbonylaminobutyric acid the corresponding protected diamino-, triamino- or tetramino-acids having a propionic chain (which are prepared with methyl acrylate, in an analogous way to the publication *Tetrahedron* 2006, 62, 8335), compounds 8, 10, 12, 13, 14, 29, 30, 27, 28, 58, 19, 20 and 18 of the formula 1 (wherein A=CO(CH$_2$)$_n$, n=2) have been synthesized.

Example 9

Preparation of 2-{3-[4-(3-aminopropylamino)-butylamino]-propylamino}-ethanesulfonic acid 3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-amide or (4-β-2-{3-[4-(3-aminopropylamino)-butylamino]-propylamino}-ethanesulfonamido-4'-demethyl-4-deoxypodophyllotoxin) (Compound 54)

Stage 1: Preparation of 4-β-vinylsulfonylamino-4'-benzyloxycarbonyl-4'-demethyl-4-deoxypodophyllotoxin 500 mg of 4β-amino-4-deoxy-4'-benzyloxycarbonyl-4'-demethylepipodophyllotoxin of the formula 8 are dissolved in 20 mL of CH$_2$Cl$_2$ with 0.4 mL of triethylamine. 0.1 mL of 2-chloroethanesulfonyl chloride in 5 mL of CH$_2$Cl$_2$ is added dropwise with stirring at −15° C. Stirring is continued for 15 min and then the mixture is left to return to ambient temperature, and stirring is continued for 4 hrs. The reaction mixture is then poured into water and extracted with CH$_2$Cl$_2$. The organic phases are combined, dried over Na$_2$SO$_4$, filtered and evaporated. The residue is purified by flash chromatography, eluted with a gradient of pure heptane to pure AcOEt. The pure fractions obtained are evaporated to yield 220 mg of a foam. Yield=55%. TLC SiO$_2$ (90:9:1 CH$_2$Cl$_2$:MeOH:NH$_4$OH) Rf 0.7, $^1$H-NMR (DMSO) δ 8.03 (d, 1H, J=8.56 Hz, NH), 7.40 (m, 5H, Ar), 7.02 (dd, 1H, J=16.36 Hz, J'=9.8 Hz, HC=), 6.91 (s, 1H, H$_5$), 6.53 (s, 1H, H$_8$), 6.33 (s, 2H, H$_2$', H$_6$'), 6.15 (d, 1H, J=16.4 Hz, HC=), 6.09 (d, 1H, J=9.8 Hz, HC=), 6.01 (d, 2H, J=11.3 Hz, OCH$_2$O), 5.23 (s, 2H, CH$_2$Ph), 4.67 (dd, 1H, J=8.24 Hz, J'=4.4 Hz, H$_4$), 4.59 (d, 1H, J=5.4 Hz, H$_1$), 4.31 (t, 1H, J=8.04 Hz, H$_{11a}$), 4.13 (t, 1H, H$_{11b}$), 3.63 (s, 6H, OMe), 3.28 (dd, 1H, J=5.36 Hz and J'=18.48 Hz, H$_2$), 2.97 (m, 1H, H$_3$).

Stage 2: Addition of N1,N2,N3-tribenzyloxycarbonylspermine 220 mg of the vinyl derivative obtained from the above stage are dissolved in 10 mL of methanol. 220 mg of N1,N2,N3-tribenzyloxycarbonylspermine are added to the reaction mixture, and stirring is continued for 5 days at room temperature. After evaporation under vacuum, water is added, and the mixture is extracted with ethyl acetate. After drying of the organic phase, filtration and evaporation, a purification is carried out by flash chromatography (gradient elution from pure heptane to pure AcOEt and then to 90:9:1 AcOEt:MeOH:NH$_4$OH). 70 mg of the tetraprotected addition compound is obtained, i.e. with a 16% yield (trans-lactone compound). Another 2-epimer compound is also obtained (cis-lactone compound).

Analyses of the trans-lactone compound: TLC SiO$_2$ (90:9:1 CH$_2$Cl$_2$:MeOH:NH$_4$OH) Rf 0.6. Analytical HPLC: X Bridge C8 4.6×250 mm, 5μ, eluent: 80:20 CH$_3$CN:H$_2$O—KH$_2$PO$_4$ 6.8 g/L pH=4, flow rate 1 mL/min, RRT=3.55 min. MS (ESI+) m/z=1094.

Stage 3: Hydrogenolysis of Protecting Groups 70 mg of the trans-lactone derivative obtained above are placed under hydrogen atmosphere, in a mixture of 10 mL of methanol and 5 mL of CH$_2$Cl$_2$. 0.25 mL of HCl isopropanol are also added, together with 50 mg of 10% palladium on carbon. Vigorous stirring is continued for 5 hrs. The catalyst is filtered, washed with methanol, the residue is evaporated under vacuum and taken up with ethyl ether for crystallizing the hydrochloride, which is filtered and dried under vacuum. 30 mg of crystals are obtained as hydrochloride (Yield 63%). Mp=191° C. Analytical HPLC: X Bridge C8 4.6×250 mm, 5 g, eluent: 15:85 CH$_3$CN:H$_2$O—KH$_2$PO$_4$ 6.8 g/L pH=4, flow rate 1 mL/min, RRT=14.08 min. MS (ESI+) m/z=692 (M-H+).

Example 10

In a similar way to Example 9, compounds 51, 52, 53, 59, 60, 61, 62, and 63 can be synthesized using the corresponding protected monoamines, diamines, triamines and tetramines, by condensation with the 4-β-vinylsulfonylamino-4'-benzyloxycarbonyl-4'-demethyl-4-deoxypodophyllotoxin prepared in stage 1 of Example 9.

Example 11

Preparation of 4-{3-[4-(3-aminopropylamino)-butylamino]-propylamino}-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide or (4-β-4-{3-[4-(3-aminopropylamino)-butylamino]-propylamino}-butyramido-4'-demethyl-4-deoxypodophyllotoxin) (Compound 21)

This compound is synthesized according to either of the following 2 methods.

Method 1: Alkylation of the Chlorinated Derivative (Intermediate III):

This compound is prepared in a manner similar to Example 2. The chlorinated intermediate III prepared above is used and condensed with tribenzyloxycarbonyl-spermine (described in *Tet. Let.* 1998, 39, 439) to provide the 4-β-4-{3-[4-(3-aminopropylamino)-butylamino]-propylamino}-butyramido-4'-demethyl-4-deoxypodophyllotoxin, after hydrogenolysis according to the same method as in stage 3 of Example 9.

Method 2: Peptide Coupling:
Stage 1:
7.51 g of tribenzyloxycarbonyl spermine (triZ-spermine) (*Tet. Let.* 1998, 39, 439) are dissolved in 150 mL of acetonitrile with stirring. 2.1 mL of triethylamine are added followed with 2.25 g of methyl bromobutyrate, and then 900 mg of cesium carbonate. The reaction mixture is refluxed for 20 hrs with stirring. The medium is poured into water and extracted with ethyl acetate (3×200 mL), and the organic phases are dried over Na$_2$SO$_4$, filtered and evaporated. The residue is flash chromatographed on SiO$_2$ (gradient elution from pure CH$_2$Cl$_2$ to a mixture of 70% CH$_2$Cl$_2$ and 30% of a 9:1 MeOH:NH$_4$OH mixture). 2.48 g of the mono alkylation ester of the spermine derivative are isolated: the methyl 4-[3-(benzyloxycarbonyl-{4-[benzyloxycarbonyl-(3-benzyloxycarbonylaminopropyl)-amino]butyl}-amino)-propylamino]-butyrate of the formula 12a (as a methyl ester, wherein B=H), Formula 12a MeOOC~~~N(B)~~~N(Z)~~~N(Z)~~~NH(Z)

TLC SiO$_2$ (90:9:1 CH$_2$Cl$_2$:MeOH:NH$_4$OH) Rf=0.4. Other chromatography fractions contain the dialkylation derivative of the spermine derivative.

Stage 2:

2.48 g of this mono alkylated intermediate from Stage 1 are placed in 30 mL of acetonitrile together with 0.45 mL of triethylamine. 0.55 mL of benzyl chloroformate in 5 mL of acetonitrile is added dropwise with stirring at room temperature, and the mixture is left under stirring for 2 hrs. The reaction mixture is poured into water and extracted with ethyl acetate, and the organic phases are dried over $Na_2SO_4$, filtered and evaporated. A flash chromatography is performed (gradient elution from pure $CH_2Cl_2$ to a mixture consisting of 90% $CH_2Cl_2$ and 10% 9:1 MeOH:$NH_4OH$). 0.95 g of the tetra protected spermine derivative is obtained: the methyl 4-{benzyloxycarbonyl-[3-(benzyloxycarbonyl-{4-[benzyloxycarbonyl-(3-benzyloxycarbonylaminopropyl)-amino]-butyl}-amino)-propyl]-amino}-butyrate, corresponding to the formula 12a, wherein B=Z, as a colorless oil. Yield 32%. TLC $SiO_2$ (90:10:1 $CH_2Cl_2$:MeOH:$NH_4OH$) Rf=0.79. $^1$H-NMR (DMSO) δ 7.32 (m, 21H, NH and 4Ph), 5.03 and 5.00 (2s, 8H, benzyl $CH_2$), 3.54 (m, 3H, OMe), 3.14 (m, 12H, $CH_2N$), 2.97 (m, 2H, $CH_2N$), 2.27 (m, 2H, $CH_2CO$), 1.62-1.67 (m, 6H, $CH_2$), 1.37 (m, 2H, $CH_2$).

Stage 3:

The above ester (0.95 g) is placed under reflux with stirring in 60 mL of a 50:50 MeOH:water mixture and in the presence of 1.7 mL of 1N NaOH for 1 hr. After cooling, it is acidified with 1N HCl to pH=2, and extracted with ethyl acetate, to yield the corresponding carboxylic acid: the 4-{benzyloxycarbonyl-[3-(benzyloxycarbonyl-{4-[benzyloxycarbonyl-(3-benzyloxycarbonylaminopropyl)-amino]-butyl}-amino)-propyl]-amino}-butyric acid as a colorless oil, with a quantitative yield. TLC $SiO_2$ (95:5 $CH_2Cl_2$:MeOH) Rf=0.32. $^1$H-NMR (DMSO) δ 7.32 (m, 21H, NH and 4Ph), 4.99 and 5.04 (2s, 8H, benzyl $CH_2$), 3.14 (m, 12H, $CH_2N$), 2.97 (m, 2H, $CH_2N$), 2.15 (m, 2H, $CH_2CO$), 1.66 (m, 6H, $CH_2$), 1.37 (m, 4H, $CH_2$). ESI-MS m/z=825 M-H+.

Stage 4:

510 mg of 4β-amino-4'-demethyl-4-deoxypodophyllotoxin, the intermediate I obtained as mentioned above, are dissolved in 20 mL of acetonitrile in the presence of 950 mg of the acid obtained from the above stage and 0.34 mL of triethylamine. 370 mg of TBTU are added in one portion and stirring is continued at room temperature for 2 hrs. The reaction mixture is poured into water and extracted with ethyl acetate, the organic solution is washed with b, dried, filtered, and evaporated. The residue is purified by flash chromatography (elution with 90:10 $CH_2Cl_2$:MeOH) and then by preparative HPLC (X Bridge, C18, 10 OBD, 30×250 mm), gradient elution $CH_3CN$:$H_2O$ from 10:90 to 50:50. 430 mg (Yield 30%) of the protected spermine podophyllotoxin derivative are obtained. $^1$H-NMR (DMSO) δ 8.23 (d, 1H, J=8.16 Hz, NH), 7.32 (m, 4 Ph), 6.78 (s, 1H, $H_5$), 6.52 (s, 1H, $H_8$), 6.23 (s, 2H, $H_{2'}$, $H_{6'}$), 5.98 (d, 2H, J=17.08 Hz, $OCH_2O$), 5.19 (dd, 1H, $H_4$), 4.99 and 5.03 (2s, 8H, $CH_2$ benzyl), 4.49 (d, 1H, J=4.8 Hz, $H_1$), 4.29 (t, 1H, J=7.2 Hz, $H_{11a}$), 3.73 (m, 1H, $H_{11b}$), 3.62 (s, 6H, OMe), 3.15 (m, 13H, $CH_2N$ and $H_2$), 2.96 (m, 3H, $CH_2N$ and $H_3$), 2.10 (m, 2H, $CH_2CO$), 1.61-1.68 (m, 6H, $CH_2$), 1.37 (m, 4H, $CH_2$).

Stage 5:

The thus purified tetrabenzyloxycarbonylated compound (430 mg) is dissolved in a mixture of methanol (20 mL) and $CH_2Cl_2$ (10 mL). 5 equivalents of an HCl isopropanol solution are added. The medium is placed under hydrogen atmosphere in the presence of 50 mg of 10% palladium on carbon under vigorous stirring for 8 hrs. The catalyst is filtered, rinsed with methanol, and then the filtrate is evaporated. The residue is chromatographed on preparative HPLC (column Xbridge C18, 10μ, OBD, 30×250 mm) eluting with a 5 mM HCl solution. The fractions containing the compound are freeze dried, to obtain 115 mg of a white solid. Mp=229° C. Analytical purity: 98.25% (anal HPLC Xbridge C8, elution with 15:85 $CH_3CN$:$H_2O$—$KHPO_4$ 6.8 g/l at pH=4).

$^1$H-NMR (DMSO) δ 8.47 (d, 1H, J=8.28 Hz, NH), 6.78 (s, 1H, $H_5$), 6.53 (s, 1H, $H_8$), 6.23 (s, 2H, $H_{2'}$, $H_{6'}$), 6.00 (d, 2H, J=10.2 Hz, $OCH_2O$), 5.19 (dd, 1H, J=7.72 Hz, J'=4.68 Hz, $H_4$), 4.49 (d, 1H, J=4.96 Hz, $H_1$), 4.29 (t, 1H, J=7.8 Hz, $H_{11a}$), 3.75 (t, 1H, J=9.8 Hz, $H_{11b}$), 3.62 (s, 6H, OMe), 3.24 (dd, 2H, J=14.28 Hz, J'=4.8 Hz, $H_2$), 2.89-3.00 (m, 15H, $H_3$ and $CH_2N$), 2.29 (m, 2H, $CH_2CO$), 1.88-2.08 (m, 6H, $CH_2$), 1.73 (m, 4H, $CH_2$).

Example 12

In the same manner as described in Example 11, following Method 2 by peptide coupling, the following compounds of the formula 1 are prepared (wherein A=CO($CH_2$)$_n$, n=3, 4, or 5): 2, 4, 6, 15, 16, 17, 33, 34, 32, 31, 37, 38, 35, 36, 22, 23, 25, 26, 24, 9, 11, 55, and 56, using the corresponding protected monoamines, diamines, triamines or tetramines, which have been grafted, such as indicated in Stage 1 of Example 11, Method 2, with ethyl bromobutyrate or ethyl bromopropionate. The protection (Stage 2), saponification (Stage 3), coupling (Stage 4) and deprotection (Stage 5) stages are performed in the same manner.

Example 13

Preparation of 1-{3-[4-(3-aminopropylamino)-butylamino]-propyl}-3-[9-(4-hydroxy-3,5-dimethoxyphenyl)-8-oxo-5,5a,6,8,8a,9-hexahydrofuro-[3',4':6,7] naphtho[2,3-d][1,3]dioxol-5-yl]-urea (Compound 48)

Stage 1: Preparation of 4β-chloroacetamido-4'-demethyl-4'-benzyloxycarbonyl-4-deoxypodophyllotoxin 19.6 g of 4β-chloroacetamido-4'-demethyl-4-deoxypodophyllotoxin of the formula 4a (X=Cl, n=1) prepared in stage 1 of intermediate I, are dissolved in 400 mL of THF then 10 mL of pyridine are added. 6.5 mL of benzyl chloroformate dissolved in 50 mL of THF are then added with stirring at room temperature. The reaction mixture is stirred at ambient temperature for 6 hrs. At the end of the reaction, the solution is poured into 300 mL of 1N HCl then extracted with ethyl acetate (2×200 mL). The organic phases are dried over $Na_2SO_4$, filtered and evaporated to provide 27.9 g of the intermediate crude compound. TLC (95:5 $CH_2Cl_2$:MeOH) Rf=0.29. This intermediate is used directly in Stage 2.

Stage 2: Preparation of 4β-amino-4'-demethyl-4'-benzyloxycarbonyl-4-deoxypodophyllotoxin 27.9 g of the intermediate prepared in Stage 1, above, are dissolved in 120 mL of dimethylacetamide, 24 mL of acetic acid and 24 mL of water. This is heated to 80° C. with stirring. At this stage thiourea is added (4.81 g), and the reaction is maintained at this temperature for 12 hrs. After cooling, the reaction mixture is poured slowly into a saturated solution of $NaHCO_3$ (500 mL). It is then extracted with ethyl acetate (200 mL) and the organic phases are washed with a saturated solution of $NaHCO_3$ and then with a saturated solution of NaCl. The organic phases are separated, dried over $Na_2SO_4$, filtered and evaporated. The residue is flash chromatographed (gradient pure heptane, $CH_2Cl_2$ to 90:10 $CH_2Cl_2$:MeOH) to yield 13.8 g of 4β-amino-4'-demethyl-4'-benzyloxycarbonyl-4-deoxypodophyllotoxin of the formula 8. Yield over the 2 stages=63%. TLC (95:5 $CH_2Cl_2$:MeOH) Rf 0.55.

Stage 3: Preparation of 1-{3-[4-(3-tert-butoxycarbonylaminopropyl)-tert-butoxycarbonylaminobutyl]-tert-butoxycarbonylaminopropyl}-3β-[9-(4-benzyloxycarbonyloxy-3,5-dimethoxyphenyl)-8-oxo-5,5a,6,8,8a,9-hexahydrofuro[3',4':6,7]naphtho[2,3-d][1,3]dioxol-5-yl]-urea

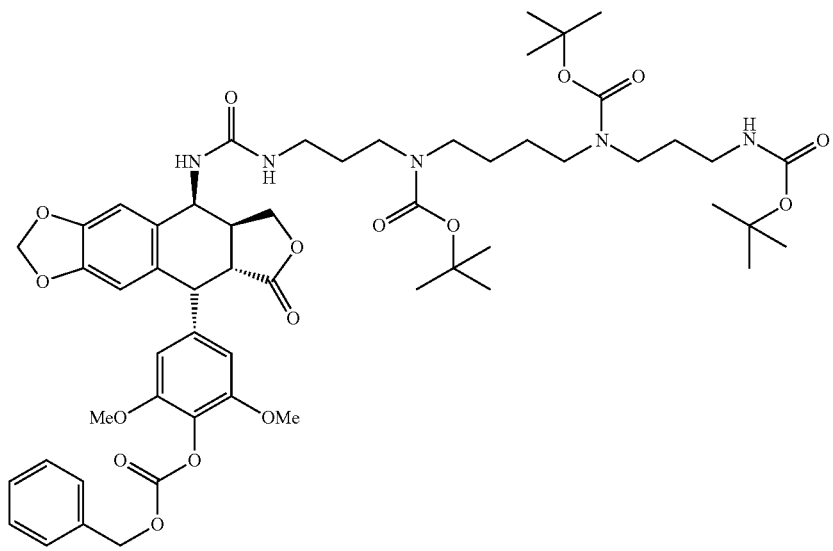

500 mg of the intermediate obtained in Stage 2 above are dissolved with stirring in 30 mL of $CH_2Cl_2$ together with 0.13 mL of triethylamine. Under stirring at 0° C., a solution of 100 mg of triphosgene in 20 mL of $CH_2Cl_2$ is added under nitrogen atmosphere. After reaching room temperature, a solution of 500 mg of triBOC spermine (*Tet.* 2000, 56, 2449) and 0.13 mL of triethylamine, in 20 mL of $CH_2Cl_2$, are added dropwise. The reaction mixture is stirred at room temperature for 3 hrs. The reaction mixture is then poured into a saturated $NaHCO_3$ solution and then extracted with $CH_2Cl_2$. The organic phases are dried over $Na_2SO_4$, filtered and evaporated. The residue is flash chromatographed on $SiO_2$ (eluting with pure $CH_2Cl_2$ to 90:10 $CH_2Cl_2$:MeOH), to yield 370 mg of a yellow oil. Yield 37%. TLC $SiO_2$ ($CH_2Cl_2$:MeOH 90:10) Rf 0.65. $^1$H-NMR (DMSO) δ 7.4 (s, 5H, arom. H), 6.81 (s, 1H, $H_5$), 6.53 (s, 1H, $H_8$), 6.35 (s, 2H, $H_{2'}$, $H_{6'}$), 5.98 (d, 2H, J=7 Hz, $OCH_2O$), 5.23 (s, 2H, $CH_2Ar$), 5.03 (dd, 1H, $H_4$), 4.60 (d, 1H, J=5.2 Hz, $H_1$), 4.32 (t, 1H, J=7.6 Hz, $H_{11a}$), 3.81 (t, 1H, J=10 Hz, $H_{11a}$), 3.63 (s, 6H, OMe), 2.87 (m, 14H, $H_2$, $H_3$, $CH_2N$), 1.56 (m, 2H, $CH_2$), 1.37 (m, 33H, $CH_2$, $CH_3$).

Stage 4: Preparation of 1-{3-[4-(3-tert-butoxycarbonylaminopropyl)-tert-butoxycarbonylaminobutyl]-tert-butoxycarbonylaminopropyl}-3-[9-(4-hydroxy-3,5-dimethoxyphenyl)-8-oxo-5,5a,6,8,8a,9-hexahydrofuro[3',4':6,7]naphtho[2,3-d][1,3]-dioxol-5-yl]-urea

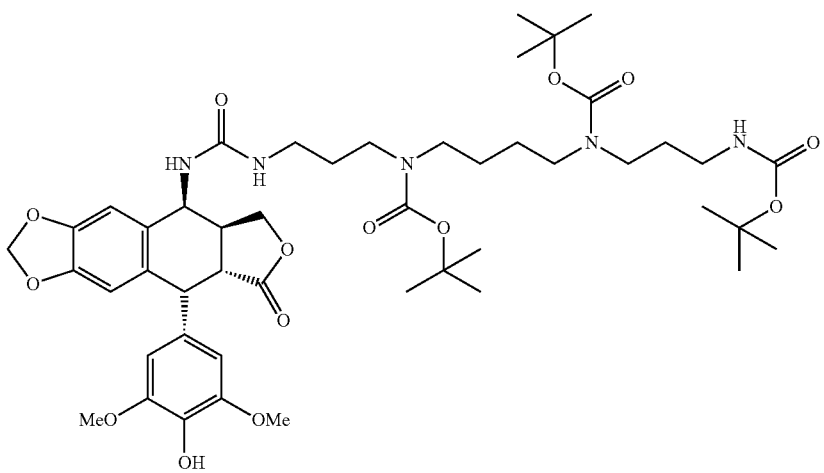

740 mg of protected (triBOC and 4′O-benzyloxycarbonyl) intermediate obtained in Stage 3 above are dissolved in 20 mL of methanol with 100 mg of 10% palladium on carbon with stirring and under hydrogen atmosphere for 2 hrs, with vigorous stirring. The solution is filtered from the catalyst, washed with MeOH and then evaporated to dryness. The residue is flash chromatographed on $SiO_2$ (gradient $CH_2Cl_2$ to 90:10 $CH_2Cl_2$:MeOH) followed with preparative HPLC (X Bridge, OBD, C18, 10μ, 30×250 mm), eluting with 20:80 $CH_3CN:H_2O$ up to 100% $CH_3CN$. Extraction of the fractions containing ethyl acetate, drying over $Na_2SO_4$, filtration and evaporation, give 630 mg of 1-{3-[4-(3-tert-butoxycarbonylaminopropyl)-tert-butoxycarbonylamino-butyl]-tert-butoxycarbonylaminopropyl}-3-[9-(4-hydroxy-3,5-dimethoxyphenyl)-8-oxo-5,5a,6,8,8a,9-hexahydrofuro[3′,4′:6,7]naphtho[2,3-d][1,3]dioxol-5-yl]-urea as a colorless oil. Yield 97%. TLC $SiO_2$ (90:10:1 $CH_2Cl_2$:MeOH:$NH_4OH$) Rf 0.58.

Stage 5: Preparation of 1-{3-[4-(3-aminopropylamino)-butylamino]-propyl}-3-[9-(4-hydroxy-3,5-dimethoxyphenyl)-8-oxo-5,5a,6,8,8a,9-hexahydrofuro[3′,4′:6,7]-naphtho[2,3-d][1,3]dioxol-5-yl]-urea

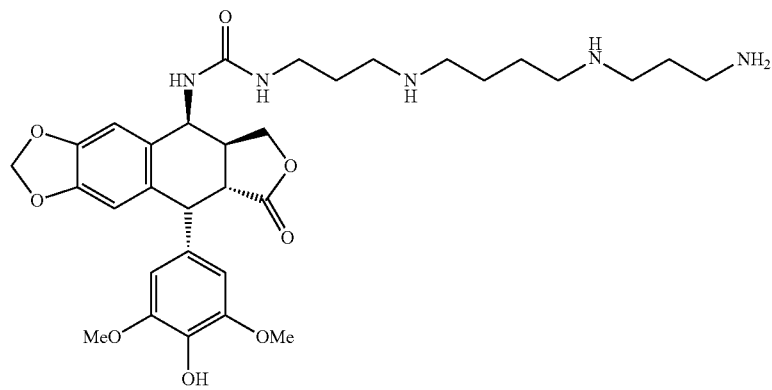

630 mg of the triBOC intermediate above are dissolved in 10 mL of HCl isopropanol (3M) and then left under stirring for 6 hrs at room temperature. The medium is evaporated to dryness and then taken up with ethanol. The hydrochloride precipitate formed is filtered, washed with absolute ethanol and with ethyl ether. 391 mg of salt is obtained, i.e. a 78% yield. TLC $SiO_2$ (40:40:20 $CH_2Cl_2$:MeOH:$NH_4OH$) Rf=0.55. Mp=166° C. HPLC Purity 97% (analytical HPLC X Bridge, 15:85 $CH_3CN:H_2O$:6.8 g/l $KH_2PO_4$— pH=4, RT=8.08). ESI-MS, m/z=628 (M-H+). Anal. $C_{32}H_{45}N_5O_8$, 3HCl, 4.4$H_2O$=813.39 calc. C %, 52.14; H %, 6.56; N %, 9.50, found C %, 51.89, H %, 5.95, N % 9.58. $^1$H-NMR (DMSO, $D_2O$) δ 6.82 (s, 1H, $H_5$), 6.52 (s, 1H, $H_8$), 6.24 (s, 2H, $H_2$, $H_6$), 5.98 (d, 2H, J=10 Hz, $OCH_2O$), 5.01 (d, 1H, J=4 Hz, $H_4$), 4.51 (d, 1H, J=4.8 Hz, $H_1$), 4.35 (t, 1H, J=8 Hz, $H_{11a}$), 3.84-3.94 (m, $H_{11a}$, $H_2O$), 3.63 (s, 6H, OMe), 3.17 (m, 3H, H2, $CH_2N$), 2.95 (m, 11H, H3, $CH_2N$), 1.94 (m, 2H, $CH_2$), 1.76 (m, 2H, $CH_2$), 1.68 (m, 2H, $CH_2$).

Example 14

In the same manner as described in Example 13, compounds 39, 40, 41, 42, 43, 47, and 48 can be prepared following the same procedure as described in Stage 3, but using the corresponding protected diamines, triamines, and tetramines. The deprotection steps are performed as described in Stage 4 with regard to hydrogenolysis of the groups Z, or as described in Stage 5 with regard to cleavage of BOC groups.

Example 15

The urea compounds 44, 45, and 49 are prepared according to Example 2 by alkylation but using the protected triamines or tetramines in place of dimethylamine, and the 1-chloroethyl-3-[9-(4-hydroxy-3,5-dimethoxyphenyl)-8-oxo-5,5a,6,8, 8a,9-hexahydrofuro[3′,4′:6,7]naphtho[2,3-d][1,3]dioxol-5-yl]-urea derivative (disclosed in *Heterocycles* 1994, 39, 361) in place of intermediate III. The deprotection stages are performed in the same manner as described in Example 13, in Stage 4 and Stage 5.

Example 16

The urea compounds 46, 47, 64, 65, 66, 67, and 68 are prepared according to the procedure described in Stage 3 of Example 13, but using the 3-chloropropylisocyanate, the 4-chlorobutylisocyanate, the 5-chloropentylsiocyanate (*Bull. Soc. Chim. Fr.* 1959, 611), in place of triphosgene, to lead to the corresponding alkyl ureas. The following stages are conducted as indicated in Example 15.

Example 17

Compound 50:1-[3-{3-[4-(3-Aminopropylamino)-butylamino]-propylamino}-propyl]-3-[9-(4-hydroxy-3,5-dimethoxyphenyl)-8-oxo-5,5a,6,8,8a,9-hexahydrofuro[3′,4′: 6,7]naphtho[2,3-d][1,3]dioxol-5-yl]-urea is also prepared according to the principle of the process disclosed in Example 13, but using the appropriate reactant.

Stage 1: Preparation of (3-tert-butoxycarbonylaminopropyl)-[4-(tert-butoxycarbonyl-{3-[3-(1,3-dioxo-1,3-dihydroisoindol-2-yl)propylamino]-propyl}-amino)-butyl]-carbamic acid tertiary-butyl ester

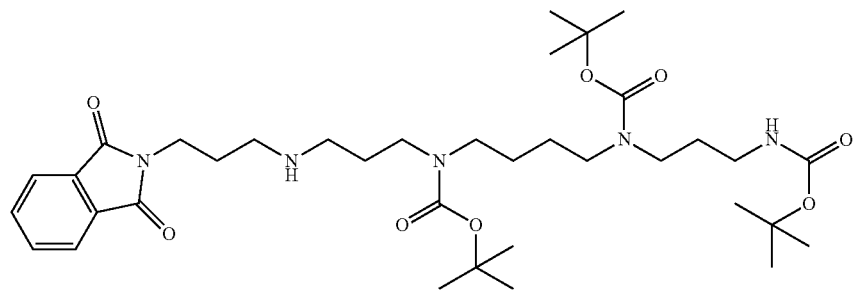 [SMILES: CC(C)(C)OC(=O)NCCCN(CCCCN(CCCNCCCN1C(=O)c2ccccc2C1=O)C(=O)OC(C)(C)C)C(=O)OC(C)(C)C]

A solution of triBOC spermine (*Tet.* 2000, 56, 2449) (6 g, 11.2 mmol, 1 eq) in 100 mL of acetonitrile is added with N-(3-bromopropyl)phthalimide (3 g, 11.2 mmol, 1 eq) and cesium carbonate (7.2 g, 22.4 mmol, 2 eq). The medium is refluxed with stirring for 8 hrs. After evaporation, it is poured into water (400 mL) and extracted with AcOEt (3×200 mL). The organic phases are washed with a saturated aqueous NaCl solution, separated, dried over $Na_2SO_4$ and evaporated. The residue is flash chromatographed on $SiO_2$ and eluted with a gradient of pure $CH_2Cl_2$ to $CH_2Cl_2$:MeOH:$NH_4OH$ (80:18:2) to yield after evaporation 2.31 g of a colorless oil (Yield 30%). TLC $SiO_2$ (90:9:1 $CH_2Cl_2$:MeOH:$NH_4OH$) Rf=0.5. MS: m/z=690 (M-H+).

Stage 2: Preparation of [3-(tert-butoxycarbonyl-{4-[tert-butoxycarbonyl-(3-tert-butoxycarbonylaminopropyl)-amino]-butyl}-amino)-propyl]-[3-(1,3-dioxo-1,3-dihydro-isoindol-2-yl)-propyl]-carbamic acid tertiary-butyl ester

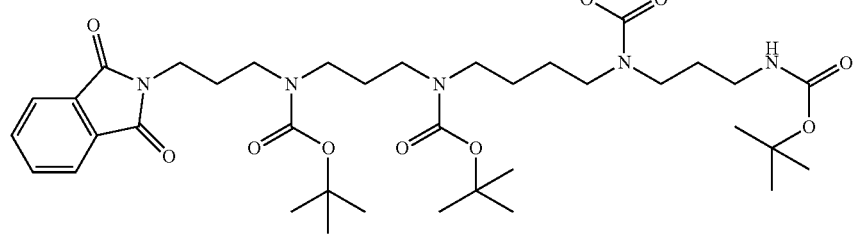

The compound obtained in Stage 1 above (2.31 g, 3.3 mmol, 1 eq) is dissolved in 50 mL of THF with stirring. A solution of $BOC_2O$ (0.8 g, 3.7 mmol, 1.1 eq) in 10 mL of THF is then added dropwise at room temperature. Stirring is continued for 4 hrs and then the medium is poured into water and extracted with AcOEt (3×100 mL), dried ($Na_2SO_4$), filtered, and evaporated. The residue is flash chromatographed with a gradient from pure heptane to pure AcOEt. 1.49 g (Yield 56%) is obtained after evaporation.

Stage 3: Preparation of (3-aminopropyl)-[3-(tert-butoxycarbonyl-{4-[tert-butoxycarbonyl-(3-tert-butoxycarbonylaminopropyl)-amino]-butyl}-amino)-propyl]carbamic acid tertiary-butyl ester (Aminopropyl tetraBOC spermine)

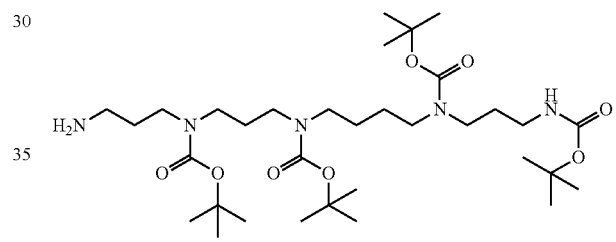

The compound from Stage 2 above (1.49 g, 1.88 mmol, 1 eq) is refluxed in 50 mL of EtOH in the presence of hydrazine hydrate (0.5 mL, 16.1 mmol, 8.5 eq) for 6 hrs. The cooled medium is filtered, washed with EtOH, and evaporated. The residue is flash chromatographed on $SiO_2$ (gradient elution pure $CH_2Cl_2$ up to 80:18:2 $CH_2Cl_2$:MeOH:$NH_4OH$). After evaporation of the pure fractions, 1.09 g of a colorless oil is obtained (yield 88%). TLC $SiO_2$ (90:9:1 $CH_2Cl_2$:MeOH:$NH_4OH$) Rf=0.34. MS: m/z=660 (M-H+).

Stage 4: Coupling of aminopropyl tetraBOC spermine with 4β-amino-4'-demethyl-4'-benzyloxycarbonyl-4-deoxypodophyllotoxin

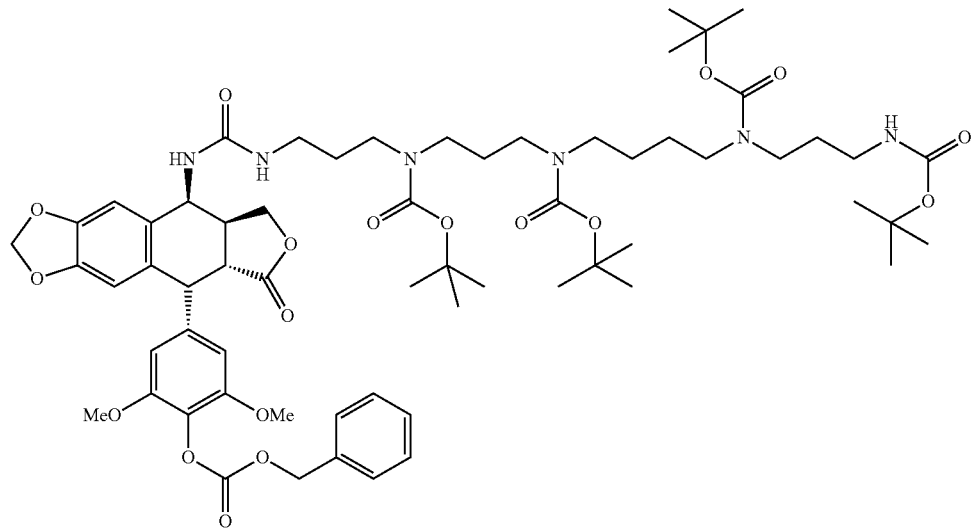

The 4β-amino-4'-demethyl-4'-benzyloxycarbonyl-4-deoxypodophyllotoxin obtained in Stage 2 of Example 13 (0.88 g, 1.6 mmol, 1 eq) is dissolved with stirring in 100 mL of $CH_3CN$, together with 0.23 mL (1.6 mmol, 1 eq) of triethylamine, and cooled to 0° C. A solution of triphosgene (0.17 g, 0.58 mmol, 0.35 eq) is then added dropwise. After reaching room temperature a solution of the mixture of the intermediate compound aminopropyl tetraBOC spermine, obtained in Stage 3 above (1.09 g, 1.6 mmol, 1 eq) and of 0.23 mL (1.6 mmol, 1 eq) of triethylamine in 30 mL of $CH_2Cl_2$ is then added dropwise. After stirring for 3 hrs, the mixture is poured into a $NaHCO_3$ solution, and extracted with $CH_2Cl_2$ (3×100 mL). The organic phases are separated, dried over $Na_2SO_4$, filtered and evaporated to yield a residue which is purified by flash chromatography (gradient from pure $CH_2Cl_2$ to 90:10 $CH_2Cl_2$:MeOH). After evaporation 1.37 g (68%) of the protected urea derivative is obtained as a white foam. TLC $SiO_2$ (95:5 $CH_2Cl_2$:MeOH) Rf=0.62. Analytic HPLC: column Xbridge C8, 5μ, 4.6×250 mm, eluting with 80:20 $CH_3CN:H_2O$, RRT=7.7 min.

Stage 5: Deprotection of the 4'-position

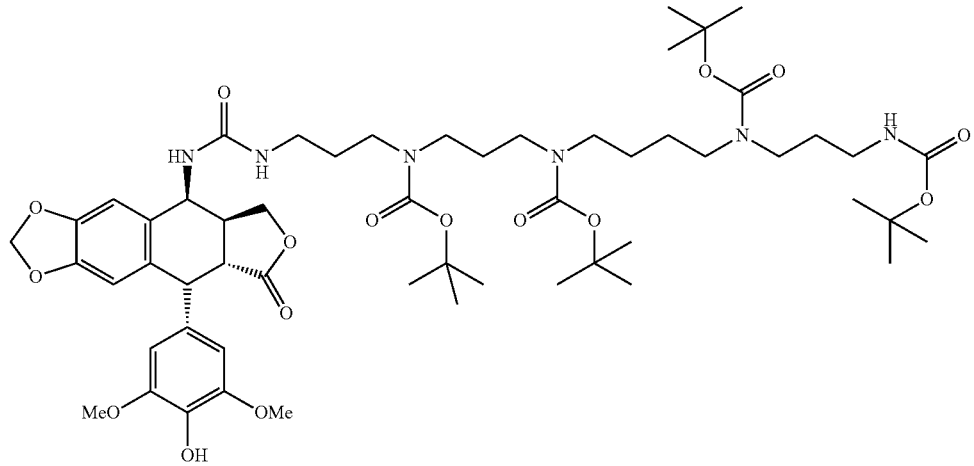

The derivative obtained in Stage 4 (1.37 g) is hydrogenolysed with 50 mg of 10% palladium on carbon in 100 mL of MeOH under vigorous stirring for 8 hrs. The catalyst is filtered and the filtrate is evaporated to dryness. The residue is first purified by flash chromatography on $SiO_2$ eluting with a gradient from pure heptane to pure AcOEt, and then by HPLC (X bridge C18 OBD 30×250 mm), with a gradient from 50:50 $CH_3CN:H_2O$ to pure $CH_3CN$. 0.95 g (yield=78%) of the compound deprotected in the 4'-position is obtained. TLC $SiO_2$ (95:5 $CH_2Cl_2$:MeOH) Rf=0.33. Analytic HPLC: column Xbridge C8, 5μ, 4.6×250 mm, eluting with 80:20 $CH_3CN:H_2O$, RRT=4.7 min Stage 6: Preparation of 1-[3-{3-[4-(3-Aminopropylamino)-butylamino]-propylamino}-propyl]-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea via deprotection of BOC groups

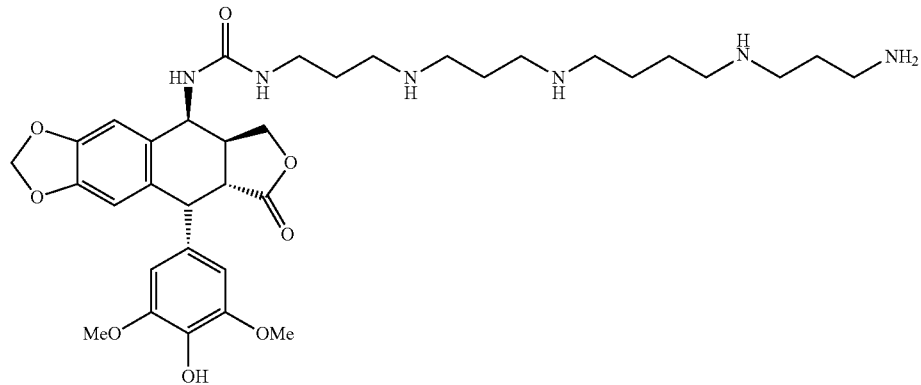

The compound obtained in Stage 5 above (0.95 g, 0.72 mmol) is dissolved in 10 mL of $CH_2Cl_2$ in the presence of 10 mL of HCl-isopropanol (3M) with stirring for 4 hrs. The resulting precipitate is filtered and then rinsed with $Et_2O$ to yield 0.6 g (94%) of a white powder of 1-[3-{3-[4-(3-aminopropylamino)-butylamino]-propylamino}-propyl]-3-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-urea. Mp=213° C. MS: m/z=685 (M-H+).

3—Pharmacological Test

Example 18

In Vitro Pharmacological Tests

A cytotoxicity test is used. It measures the cell growth inhibition of the A549 human line (non-small cell lung cancer):

The A549 tumor cells are plated in a 96-well plate in RPMI 1640 medium free of phenol red (Seromed) to which is added 5% of fetal calf serum (100 µl/well, $1.25 \times 10^4$ cells/ml). After incubation for 24 hrs at 37° C. in an incubator at 5% $CO_2$, the medium is replaced by that containing the compound to be tested, followed by incubation of the plates for another 48 hrs. Cell survival is assessed by measuring the luminescence after salting-out of the ATP from the medium using the cell lysis, luciferase and luciferine solutions included in the ATP-lite-M™ kit following the manufacturer's guidelines (Packard, Rungis, France). Each experimental condition was tested at least three times in sixplicate.

The results show that the compounds of the invention have potent cytotoxic properties. The inhibiting concentration 50 (IC50), which is the concentration of the compound to be tested providing a 50% inhibition of cell proliferation, is for example for compound 21: IC50=$1.7 \times 10^{-9}$ M, or for compound 48: IC50=$1.2 \times 10^{-8}$ M.

Example 19

In Vivo Pharmacological Tests

Experimental P388 tumor model. The model used is P388 murine leukemia (*Tumor Models in Cancer Research.* Teicher, B. A. ed., Humana Press Inc., Totowa, N.J. Pp. 23-40, 2002), which is maintained by sequential intraperitoneal transplantations in DBA/2 mice (DBA/2JIco mice, Charles River), as previously disclosed (Classic in vivo cancer models: Three examples of mouse models used in experimental therapeutics. *Current Protocols in Pharmacology* Unit 5.24: 5.24.1-5.24.16, 2001).

The experiment is carried out according to a previously disclosed protocol (*Cancer Chemother. Pharmacol.* 1998, 41, 437-447). This comprises implanting $10^6$ P388 leukemia cells per mouse into C2DF1 hybrid mice (CD2F1/CrlBR, Charles River, St Aubin-les-Elbeuf, France) intravenously at day zero. After the animals have been randomized in treatment and control cages, the compounds to be tested are administered in one single injection by intraperitoneal route the day after the tumor transplantation, at day 1. The animals are then monitored every day, weighed twice per week, and any clinical reaction is recorded. The survival rate is the parameter used to assess antitumor activity. The increase in survival rate is defined as the $T/C_{survival}$ ratio (%), which corresponds to: (Median survival rate of the treated group/Median survival rate of the control group)×100. The $T/C_{survival}$ ratio is calculated for each dosage and the largest value obtained represents the maximum increase in survival rate achieved (maximum activity), which is defined as the optimum $T/C_{survival}$ ratio.

The results show that the compounds have caused a significant increase in survival rate for animals with P388 leukemia.

As an example, compound 21 of Example 11 displays an optimum $T/C_{survival}$ value of 186%, at a dose of 0.16 mg/kg, indicating that treating the animals with this compound provided an 86% increase in survival rate of the animals. In fact, according to the NCI's (National Cancer Institute) criteria, a $T/C_{survival}$ value is regarded as significant if it is higher than at least 120% (*Semin. Oncol.* 1981, 8, 349-361).

The loss in relative body weight of the animals, combined with the optimum activity of the compounds, is highly lower than the toxicity threshold, according to the NCI's criteria (*Ann. Oncol.* 1994, 5, 415-422).

ABBREVIATIONS

APCI Atmospheric pressure chemical ionization
BOC tert-Butyloxycarbonyl
DMF Dimethylformamide
DMSO Dimethylsulfoxide
ESI Electro Spray Ionization
HPLC High Performance Liquid Chromatography
Mp Melting point
MS Mass Spectrum
NMR Nuclear Magnetic Resonance
Rf Frontal ratio
TBTU 2-(1H-Benzotriazole-1-yl)-1,1,3,3-tetramethyluronium tetrafluoroborate
THF Tetrahydrofuran
TLC Thin Layer Chromatography
Z Benzyloxycarbonyl

The invention claimed is:

1. A method for treating cancer comprising the administration to a person in need thereof of an effective amount of a compound of the general formula 1:

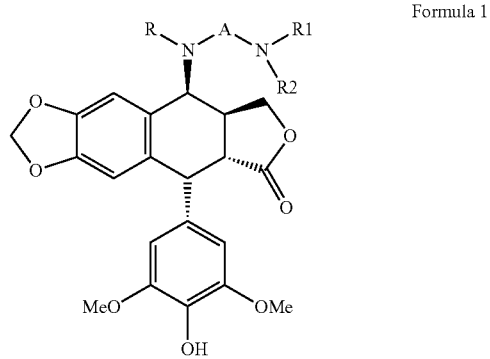

Formula 1 wherein:
R represents hydrogen or $C_{1-4}$alkyl,
A represents $CO(CH_2)_n$, or $CONH(CH_2)_n$, where n=2, 3, 4, or 5,
R1=H, or $C_{1-4}$alkyl,
R2=$(CH_2)_m$—NR3R4, where m=2, 3, 4, or 5,
R3=H, or $C_{1-4}$alkyl
R4=H, $C_{1-4}$alkyl, or $(CH_2)_p$—NR5R6, where p=2, 3, 4, or 5,
R5=H, or $C_{1-4}$alkyl, and
R6=H, $C_1$-$C_4$alkyl, or $(CH_2)_q$—$NH_2$, where q=2, 3, 4, or 5,
or a pharmaceutically acceptable salt thereof.

2. The method according to claim 1, wherein the cancer is selected from the group consisting of liquid tumors and solid tumors.

3. The method according to claim 2, wherein the solid tumor is selected from the group consisting of melanomas, colorectal cancers, lung cancers, prostate cancers, bladder cancers, breast cancers, uterus cancers, esophageal cancers, stomach cancers, pancreas cancers, liver cancers, ovarian cancers, leukemias, ENT cancers and brain cancers.

4. The method according to claim 3, wherein leukemia is selected from the group consisting of lymphomas and myelomas.

5. The method according to claim 1, wherein R=H.

6. The method according to claim 1, wherein m=3 or 4, p=3 or 4, and q=3.

7. The method according to claim 1, wherein the compound of formula 1 is selected from the following compounds:

Compound 1: 3-(2-Dimethylaminoethylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide, Compound 2: 4-(2-Dimethylaminoethylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide, Compound 3: 3-[(2-Dimethylaminoethyl)-methylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide, Compound 4: 4-[(2-Dimethylaminoethyl)-methylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide, Compound 7: 5-dimethylaminopentanoic acid N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-amide, Compound 8: 3-(2-Diethylaminoethylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide, Compound 9: 4-(2-Diethylaminoethylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide, Compound 10: 3-(2-Diethylaminopropylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide, Compound 11: 4-(2-Diethylaminopropylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide, Compound 12: 3-(2-Aminoethylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide, Compound 13: 3-(3-Aminopropylamino)-N-[9-(4-hydroxy-3,5-dimethoxyphenyl)-8-oxo-5,5a,6,8,8a,9-hexahydrofuro[3',4':6,7]naphtho[2,3-d][,3]dioxol-5-yl]-propionamide, Compound 14: 3-(4-Aminobutylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide, Compound 15: 4-(3-Aminopropylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide, Compound 16: 4-(4-Aminobutylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide, Compound 17: 5-(4-aminobutylamino)pentanoic acid N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-amide, Compound 18: 3-{3-[4-(3-Aminopropylamino)-butylamino]-propylamino}-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide, Compound 19: 3-{3-[3-(3-Aminopropylamino)-propylamino]-propylamino}-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide, Compound 20: 3-{4-[4-(4-Aminobutylamino)-butylamino]-butylamino}-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide, Compound 21: 4-{3-[4-(3-Aminopropylamino)-butylamino]-propylamino}-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide, Compound 22: 4-{3-[3-(3-Aminopropylamino)-propylamino]-propylamino}-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide, Compound 23: 4-{4-[4-(4-Aminobutylamino)-butylamino]-butylamino}-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide, Compound 24: 5-{3-[4-(3-aminopropylamino)-butylamino]-propylamino}pentanoic acid N-[9-(4-hydroxy-3,5-dimethoxyphenyl)-8-oxo-55a,6,8,8a,9-hexahydrofuro[3',4':6,7]naphtho[2,3-d][1,3]dioxol-5-yl]-amide, Compound 25: 5-{3-[3-(3-aminopropylamino)-propylamino]-propylamino}pentanoic acid N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-amide, Compound 26: 5-{4-[4-(4-aminobutylamino)-butylamino]-butylamino}pentanoic acid N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-amide, Compound 27: 3-[3-(4-Aminobutylamino)-propylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide, Compound 28: 3-[4-(3-Aminopropylamino)-butylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide, Compound 29: 3-[3-(3-Aminopropylamino)-propylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide, Compound 30: 3-[4-(4-Aminobutylamino)-butylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide, Compound 31: 4-[3-(4-Aminobutylamino)-propylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide, Compound 32: 4-[4-(3-Aminopropylamino)-butylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide, Compound 33: 4-[3-(3-Aminopropylamino)-propylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide, Compound 34: 4-[4-(4-Aminobutylamino)-butylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-butyramide, Compound 35: 5-[3-(4-Aminobutylamino)-propylamino]pentanoic acid N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-amide, Compound 36: 5-[4-(3-Aminopropylamino)-butylamino]pentanoic acid N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-amide, Compound 37: 5-[3-(3-Aminopropylamino)-propylamino]pentanoic acid N-[9-(4-hydroxy-3,5-dimethoxyphenyl)-8-oxo-5,5a,6,8,8a,9-hexahydrofuro[3',4':6,7]naphtho[2,3-d][,3]dioxol-5-yl]-amide, Compound 38: 5-[4-(4-Aminobutylamino)-butylamino]pentanoic acid N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-amide, Compound 40:1-[4-(3-Aminopropylamino)-butyl]-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea, Compound 41: 1-[3-(4-Aminobutylamino)-propyl]-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea, Compound 42: 1-[3-(3-Aminopropylamino)-propyl]-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea, Compound 43: 1-[4-(4-Aminobutylamino)-butyl]-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea, Compound 44: 1-{2-[3-(4-Aminobutylamino)-propylamino]-ethyl}-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea, Compound 45: 1-{2-[4-(3-Aminopropylamino)-butylamino]-ethyl}-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea, Compound 46: 1-{4-[4-(4-Aminobutylamino)-butylamino]-butyl}-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea, Compound 47: 1-{3-[3-(3-Aminopropylamino)-propylamino]-propyl}-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea, Compound 48: 1-{3-[4-(3-Aminopropylamino)-butylamino]-propyl}-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea, Compound 49: 1-[2-{3-[4-(3-Aminopropylamino)-butylamino]-propylamino}-ethyl]-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea, Compound 50:1-[3-{3-[4-(3-Aminopropylamino)-butylamino]-propylamino}-propyl]-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea, Compound 55: 5-[(2-Dimethylaminoethyl)-methylamino]pentanoic acid N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-amide, Compound 58: 3-(5-Aminopentylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-propionamide, Compound 64: 1-[4-{3-[4-(3-Aminopropylamino)-butylamino]-propylamino}-butyl]-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea, Compound 65: 1-(5-{3-[4-(3-Aminopropylamino)-butylamino]-propylamino}-pentyl)-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea, Compound 66: 1-{3-[3-(4-Aminobutylamino)-propylamino]-propyl}-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea, Compound 67: 1-{4-[3-(4-Aminobutylamino)-propylamino]-butyl}-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea, Compound 68: 1-{4-[4-(3-Aminopropylamino)-butylamino]-butyl}-3-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-urea, and inorganic or organic acid addition salts thereof.

8. The method according to claim 1, wherein the compound of formula 1 is used in combination with other anticancer treatments.

9. The method according to claim 8, wherein the other anticancer treatments are cytotoxic or cytostatic.

10. The method according to claim 8, wherein the other anticancer treatments use platinum derivatives, taxans, vincas, or 5-FU.

* * * * *